United States Patent
Hegre et al.

(10) Patent No.: US 11,566,246 B2
(45) Date of Patent: Jan. 31, 2023

(54) SIRT1-SARNA COMPOSITIONS AND METHODS OF USE

(71) Applicant: MINA THERAPEUTICS LIMITED, London (GB)

(72) Inventors: Siv Anita Hegre, Trondheim (NO); Pinelopi Andrikakou, London (GB); Vikash Reebye, London (GB)

(73) Assignee: MiNA Therapeutics Limited, London (GB)

( * ) Notice: Subject to any disclaimer, the term of this patent is extended or adjusted under 35 U.S.C. 154(b) by 24 days.

(21) Appl. No.: 17/046,380

(22) PCT Filed: Apr. 12, 2019

(86) PCT No.: PCT/GB2019/051061
§ 371 (c)(1),
(2) Date: Oct. 9, 2020

(87) PCT Pub. No.: WO2019/197845
PCT Pub. Date: Oct. 17, 2019

(65) Prior Publication Data
US 2021/0102204 A1    Apr. 8, 2021

Related U.S. Application Data

(60) Provisional application No. 62/656,465, filed on Apr. 12, 2018.

(51) Int. Cl.
*C07H 21/04*    (2006.01)
*C12N 15/113*   (2010.01)

(52) U.S. Cl.
CPC ........ *C12N 15/113* (2013.01); *C12N 2310/11* (2013.01); *C12N 2310/14* (2013.01); *C12N 2310/30* (2013.01)

(58) Field of Classification Search
None
See application file for complete search history.

(56) References Cited

U.S. PATENT DOCUMENTS

2021/0363525 A1\* 11/2021 Sætrom ................ A61P 11/00

FOREIGN PATENT DOCUMENTS

| WO | 2020/065662 A2 | 6/2010 |
|----|----------------|--------|
| WO | 2010/102058 A2 | 9/2010 |
| WO | 2011/005765 A1 | 1/2011 |
| WO | 2011/005786 A2 | 1/2011 |
| WO | 2011/005793 A1 | 1/2011 |
| WO | 2012/005898 A2 | 1/2012 |
| WO | 2012/177639 A2 | 12/2012 |
| WO | 2015/162422 A1 | 10/2015 |

OTHER PUBLICATIONS

International Search Report and Written Opinion dated Aug. 2, 2019 in corresponding application No. PCT/GB2019/051061 titled "SIRT1-SARNA Compositions and Methods of Use".

\* cited by examiner

*Primary Examiner* — Kimberly Chong
(74) *Attorney, Agent, or Firm* — McNeill Baur PLLC

(57) ABSTRACT

The invention relates to a saRNAs useful in upregulating the expression of the SIRT1 gene and therapeutic compositions comprising the saRNA. Methods of using the saRNA and the therapeutic compositions are also provided.

15 Claims, 1 Drawing Sheet
Specification includes a Sequence Listing.

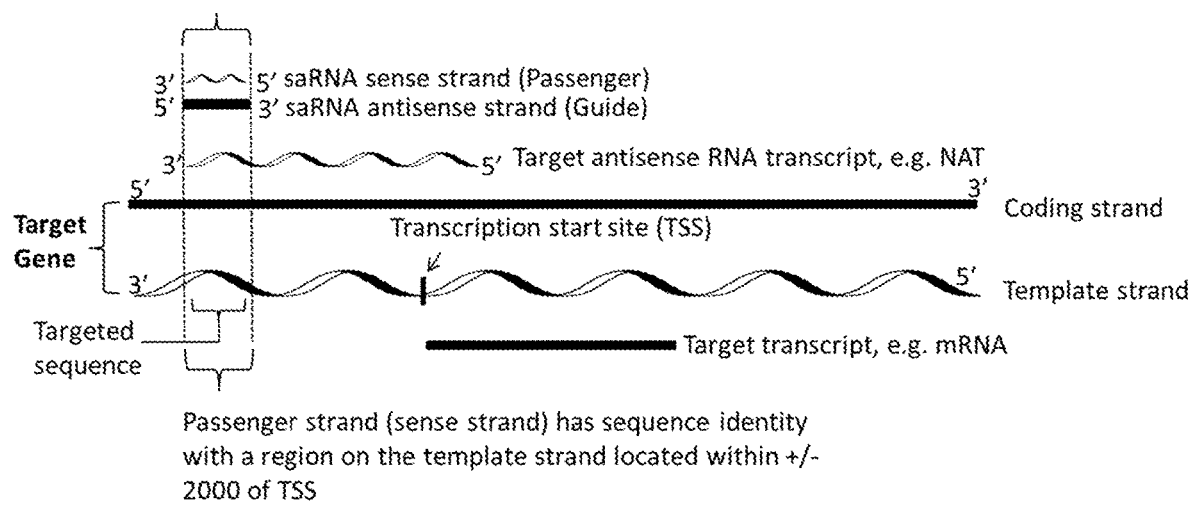

SEQUENCE LISTING

<160> NUMBER OF SEQ ID NOS: 112

<210> SEQ ID NO 1
<211> LENGTH: 4001
<212> TYPE: DNA
<213> ORGANISM: Homo sapiens

<400> SEQUENCE: 1

| | | | | | |
|---|---|---|---|---|---|
| cagaaaagat | agccgggagc | ggtggctcac | gcctctaatt | ccagagcttt | gggaggccga | 60 |
| ggcaggcgga | tcacctgagg | ttgagaattc | gagaccagcc | tgaccaacat | ggagaaatct | 120 |
| cgtctctact | aataatacaa | aaattagccg | ggcatggtgg | cgcatgcctg | taatcccaac | 180 |
| tactcaggag | gctgaggcac | gagaatggct | tgaacccggg | aagcggaggt | tgcggtgagc | 240 |
| cgagatcacg | ccattgcact | ccagcttggg | taacaagagc | gaaactccac | cttttaaaaa | 300 |
| aaaagaaaag | gaaaaaaaaa | aagaaaagat | aataatctag | ctagaatgta | tcatacaatc | 360 |
| acaaacaata | gcgttcgtga | aacgtgtaat | aaatggacat | ttacataaaa | acgtcattca | 420 |
| aatataacct | tggcaatgcg | cacgttaaac | ttacacaata | ctacaagtac | ctctgcattg | 480 |
| tttcctctat | taaataaaca | gtattaataa | cacaattatt | attaggtaaa | taataaatta | 540 |
| gtactcaact | gtgttgcttg | aaatcagggt | ctctttacta | aatcagtccc | taaaaacaca | 600 |
| tattactttt | tttttttttt | tttttgaga | cggggtctca | ctctgttgcc | caccctggag | 660 |
| tgcagtggca | ggatcacagc | tcactgcaac | ctcgaactct | agtacctggg | actaaaggtg | 720 |
| tgcgacacca | cgtcccgctt | tttttacttt | tagtagagag | gaggtctcgc | tatgttgccc | 780 |
| aggctggcct | gaaactccta | ggctcaagag | atcctcccgc | tttggcctcc | caaagtgcta | 840 |
| ggattacacg | aaagagccac | cgcgcccggc | ctgacccaaa | tattgataaa | gatgaacacc | 900 |
| tatcaaggat | agaaactcct | cagatcaaaa | ataagaaacc | tgaccgggcg | cggtggctca | 960 |
| cgcctgtaat | cccagcactt | tgggcggccg | aggcggacgg | atcacgaagt | caagaaatca | 1020 |
| agaccatcct | ggccaacatg | gtgaaacccc | gtctctgcta | aaaacacaaa | aattagctgg | 1080 |
| gcgtggtggc | gggtgtctgt | agtcccagct | actcggcagg | ctgaaggaga | atcggttgaa | 1140 |
| cgcgggaggc | ggaggttgca | ctgagccgag | atcgcgccac | tgcactccag | cctagcgaca | 1200 |
| gagcgagact | ccgtctcaaa | aaaaaaaaaa | aaaaaaaaaa | gaaaccttca | agaacatgac | 1260 |
| aactgcaaca | tatctgcttc | attatgctag | aagtgttaag | tttgtgtctc | aatactacat | 1320 |
| acatacaaaa | aaagcatgtt | tagcccaaac | accattaccg | cacaagagca | agattagaat | 1380 |
| aaaagtaata | tgaacagctc | taaaagtact | ctctctccca | tacccactcc | taactgcatt | 1440 |
| acagaatggt | aatgtcttca | ggaacagcca | cgttctttaa | attttgcaag | ctgtgactat | 1500 |
| agaaacagct | ttcctctttc | aaaaattgta | atttcagtca | taaaatata | gaccaaaaaa | 1560 |
| agcaaactgc | acaggtgtca | agtttgcaaa | aagcaattga | aaacgcagac | caacgggaca | 1620 |
| gccaaaaagt | tgcagactta | agtgtgctgg | ggggtagagg | agaaaagcaa | tgaaaataaa | 1680 |
| aaataaagaa | aaagaaaaaa | aaagctctaa | caaaagcaat | atgctaaaag | agtaagaggg | 1740 |
| ggagagaaac | ttatttttaaa | gcgactgcga | gagtctcccg | acctggctgc | tgcggaaaga | 1800 |
| acaaggccgc | ccaggcgggc | cacggacgga | ggaaaagagc | gaatccactg | gcagctcgcg | 1860 |
| cagtaggaac | cgcagccccg | gaggagcgcg | gctgaacgga | gggccggggt | ggggagggga | 1920 |
| acgccgcgga | gcctgccccg | agccccagc | cgccctcaac | ctcaggccag | taggagcccg | 1980 |
| gggagggga | ggaggagatg | cgcagttccg | gccgcccgca | ccctgcgcac | ctcggtaccc | 2040 |
| aatcgccgcc | gccgccgcct | cttcctcctc | ctcgccctcg | tcgtcgtcgt | cttcgtcgta | 2100 |

```
caagttgtcg gccagcggtg gctcccgaga tgggccctgc aggcccggcc cattgtctcc    2160
ttccccagcc gccgcagtcg cctgggcctc ttgctcccg  cctgccgccg ccgcctctgc    2220
ctccgcctcc cgccacagcg ccgccgccgc cgcacccggg cagcccctgg ccgccgccgg    2280
cacctcacgc tctggggccg ccccaccggg ctcgcccggg ctccgctcga ggccgggacc    2340
atctctccgc ggcctcttgc ggagcggctc cccggcgggg gacgacgcgg cctccctgtc    2400
ggcccccgcc gccgaggggg agccgccggg ctgaagggcg agggccgcct cgtccgccat    2460
cttccaactg cctctctggc cctcctccct cgcctcctct gctcccgctc gacgcgcggc    2520
actggcgccc ccgcggctcc ggctgcggga gatttaaacc ccatcacgtg acccgcccca    2580
tcgccgcccc cgcccctctcg gcgctcccgc cacccacgcg ggccagacca caacactacg    2640
ggtcacgtgg cgggcggagg ctgttgcgtc taccgctccg cctgggctgg aagcgcactc    2700
ggccccggcg gccggcggcc cttcctcttt gtggcgagcg tgtagtgcag ccaaattcgc    2760
ccctcggccg ctttctcaac ttctctttca aactgacctc aaatcactac cgccggaaca    2820
gctcaagttt tggtccgccc tgggaatttc cacgtcttcc tgaagtgtac acctggcctg    2880
ccttagcctt gtctatattt agctaagggt taaaacacag ctgaagctgg ctaagactta    2940
gctccctgaa atacgttgga tagtcgttct gttttgttaa taagtaggaa gagaggcaaa    3000
aggaggcggc tcctttccca ctctcctcac accgttctga cagctcctct tttgctcctt    3060
tttctgctcc ttgcttttct ccttagtcgg ttgcttttt  ccctctctc  ccatcacttg    3120
tagggtggta tacattgtaa aatccttgaa ggcatatgtc ctcctgggaa gacctttgac    3180
gtggaggttt ggagatcagc cgatctactt tctggcccca gcttggcttc aaacgtgtgt    3240
gaattccctc ctccgggcct cagttttctc acgtgcagaa tgggtttgtt gggtcagtat    3300
gagagcatgg gaaggaaatg acttggcctc catgcacatc tgcccttggt taaaatttgg    3360
agtccttcct ttctagcgtg agctatctag ccgtttctaa acttaatttt tctcatgtct    3420
taaatggtaa taagtatttt aaaacgtcat agatttaaat gagataacca gatgtaaaac    3480
gaggggtacc tagtagttca aaaggcttag tggaaagccc ttccactttc ctctctccct    3540
gaaattctgg cacactgtga ctccatatct aatcttaact aaggaccat  ataacccatg    3600
gtagatctag agccagtgtt tgttatggca tctgcctgga gcacagcgtt tctatctgtt    3660
taaaggacct ctacgagttt atggtacact gtcccttaag cctagtatgg gttctggcca    3720
tactgcatca attacctgcg tgactttagg caaccaactt aaagctgttt cttcatcctt    3780
aaaataaaaa ataaaaagct ggaaatatat cgctaaggtc ctatctacat ccaaaagtct    3840
tatttcatct ggtcaccact attcatttct gaaagtaatc atctccagtc ctagaagcct    3900
taaaaccatc tttggttgcg tggggggtcaa ggggagggag agcattagga caaatagcta   3960
atgcatgcgg gacttaaaac ctggctgggc gcggtggctg c                       4001
```

<210> SEQ ID NO 2
<211> LENGTH: 4001
<212> TYPE: DNA
<213> ORGANISM: Homo sapiens

<400> SEQUENCE: 2

```
caattattat taggtaaata ataaattagt actcaactgt gttgcttgaa atcagggtct     60
ctttactaaa tcagtcccta aaacacata  ttactttttt tttttttttt ttttgagacg    120
gggtctcact ctgttgccca ccctggagtg cagtggcagg atcacagctc actgcaacct    180
```

| | |
|---|---|
| cgaactctag tacctgggac taaaggtgtg cgacaccacg tcccgctttt tttactttta | 240 |
| gtagagagga ggtctcgcta tgttgcccag gctggcctga aactcctagg ctcaagagat | 300 |
| cctcccgctt tggcctccca agtgctagga ttacacgaaa agagccaccg cgcccggcct | 360 |
| gacccaaata ttgataaaga tgaacaccta tcaaggatag aaactcctca gatcaaaaat | 420 |
| aagaaacctg accgggcgcg gtggctcacg cctgtaatcc cagcactttg ggcggccgag | 480 |
| gcggacggat cacgaagtca agaaatcaag accatcctgg ccaacatggt gaaacccgt | 540 |
| ctctgctaaa aacacaaaaa ttagctgggc gtggtggcgg gtgtctgtag tcccagctac | 600 |
| tcggcaggct gaaggagaat cggttgaacg cgggaggcgg aggttgcact gagccgagat | 660 |
| cgcgccactg cactccagcc tagcgacaga gcgagactcc gtctcaaaaa aaaaaaaaaa | 720 |
| aaaaaaaaga aaccttcaag aacatgacaa ctgcaacata tctgcttcat tatgctagaa | 780 |
| gtgttaagtt tgtgtctcaa tactacatac atacaaaaaa agcatgttta gcccaaacac | 840 |
| cattaccgca caagagcaag attagaataa aagtaatatg aacagctcta aaagtactct | 900 |
| ctctcccata cccactccta actgcattac agaatggtaa tgtcttcagg aacagccacg | 960 |
| ttctttaaat tttgcaagct gtgactatag aaacagcttt cctcttccaa aaattgtaat | 1020 |
| ttcagtcata aaaatataga ccaaaaaaag caaactgcac aggtgtcaag tttgcaaaaa | 1080 |
| gcaattgaaa acgcagacca acgggacagc caaaaagttg cagacttaag tgtgctgggg | 1140 |
| ggtagaggag aaaagcaatg aaaataaaaa ataagaaaa agaaaaaaaa agctctaaca | 1200 |
| aaagcaatat gctaaaagag taagagggg agagaaactt attttaaagc gactgcgaga | 1260 |
| gtctcccgac ctggctgctg cggaaagaac aaggccgccc aggcgggcca cggacggagg | 1320 |
| aaaagagcga atccactggc agctcgcgca gtaggaaccg cagccccgga ggagcgcggc | 1380 |
| tgaacggagg gccggggtgg ggaggggaac gccgcggagc ctgccccgag ccccagccg | 1440 |
| ccctcaacct caggccagta ggagcccggg gagagggagg aggagatgcg cagttccggc | 1500 |
| cgcccgcacc ctgcgcacct cggtacccaa tcgccgccgc cgccgcctct tcctcctcct | 1560 |
| cgccctcgtc gtcgtcgtct tcgtcgtaca agttgtcggc cagcggtggc tcccgagatg | 1620 |
| ggccctgcag gccggcccca ttgtctcctt ccccagccgc cgcagtcgcc tgggcctctt | 1680 |
| gctccccgcc tgccgccgcc gcctctgcct ccgcctcccg ccacagcgcc gccgccgccg | 1740 |
| cacccgggca gccctggcc gccgccggca cctcacgctc tggggccgcc ccaccgggct | 1800 |
| cgcccgggct ccgctcgagg ccgggaccat ctctccgcgg cctcttgcgg agcggctccc | 1860 |
| cggcggggga cgacgcggcc tccctgtcgg ccccgccgc cgaggggag ccgccgggct | 1920 |
| gaagggcgag ggccgcctcg tccgccatct tccaactgcc tctctggccc tcctccctcg | 1980 |
| cctcctctgc tcccgctcga cgcgcggcac tggcgccccc gcggctccgg ctgcgggaga | 2040 |
| tttaaacccc atcacgtgac ccgccccatc gccgccccg ccctctcggc gctccgcca | 2100 |
| cccacgcggg ccagaccaca acactacggg tcacgtggcg ggcggaggct gttgcgtcta | 2160 |
| ccgctccgcc tgggctggaa gcgcactcgg ccccggcgg cggcggccct tcctctttgt | 2220 |
| ggcgagcgtg tagtgcagcc aaattcgccc ctcggccgct ttctcaactt ctctttcaaa | 2280 |
| ctgacctcaa atcactaccg ccggaacagc tcaagttttg gtccgccctg ggaatttcca | 2340 |
| cgtcttcctg aagtgtacac ctggcctgcc ttagccttgt ctatatttag ctaagggtta | 2400 |
| aaacacagct gaagctggct aagacttagc tccctgaaat acgttggata gtcgttctgt | 2460 |
| tttgttaata agtaggaaga gaggcaaaag gaggcggctc ctttcccact ctcctcacac | 2520 |
| cgttctgaca gctcctcttt tgctcctttt tctgctcctt gcttttctcc ttagtcggtt | 2580 |

```
gcttttttcc cctctctccc atcacttgta gggtggtata cattgtaaaa tccttgaagg    2640
catatgtcct cctgggaaga cctttgacgt ggaggtttgg agatcagccg atctactttc    2700
tggccccagc ttggcttcaa acgtgtgtga attccctcct ccgggcctca gtttctcac     2760 gtgcagaatg ggtttgttgg gtcagtatga gagcatggga aggaaatgac ttggcctcca    2820
tgcacatctg cccttggtta aaatttggag tccttccttt ctagcgtgag ctatctagcc    2880
gtttctaaac ttaattttc tcatgtctta aatggtaata agtatttaa aacgtcatag      2940 atttaaatga dataaccaga tgtaaaacga ggggtaccta gtagttcaaa aggcttagtg   3000 gaaagcccctt ccactttcct ctctccctga aattctggca cactgtgact ccatatctaa   3060
tcttaactaa ggacccatat aacccatggt agatctagag ccagtgtttg ttatggcatc   3120
tgcctggagc acagcgtttc tatctgttta aaggacctct acgagtttat ggtacactgt   3180
cccttaagcc tagtatgggt tctggccata ctgcatcaat tacctgcgtg actttaggca   3240
accaacttaa agctgtttct tcatccttaa aataaaaaat aaaaagctgg aaatatatcg   3300
ctaaggtcct atctacatcc aaaagtctta tttcatctgg tcaccactat tcatttctga   3360
aagtaatcat ctccagtcct agaagcctta aaaccatctt tggttgcgtg ggggtcaagg   3420
ggagggagag cattaggaca aatagctaat gcatgcggga cttaaaacct ggctgggcgc   3480
ggtggctgct gcctgtaatc ccagcacttt gggaggccga gcggacaga tcacctgaag    3540 tcggaagttc gagaccagcc tgaccaacat ggagaaaccc cgtctctact aaaaatacaa   3600
aattagccgg gcgtggtggc acatgcctgt aatcccagct actcagaagg ctgaggcagg   3660
agaatcgctt gaacccagca ggcagaggtt gcggtgagcc gagatcgcac cattgcacac   3720
cagcctgggc agcaagagcg aaactccgtc tcaaaaaaaa atataaataa aacctagatg   3780
aggggttgat tggtgcagca aaccaccatg gctcacctat aagtatgtaa caaacctaca   3840
cattctgcac ctgtatcctg gaacttaaat taaaaaaaaa atctttgaag cgttccttca   3900
taccaatccc tctgaaatcc atctgaccaa tcaatgacca aatcctgttg tccttccttt   3960
cttgctacac tcctcccaat tcctgactag gcaccacact c                       4001
```

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 3
gacttagctc cctgaaata                                                    19

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
gccttagcct tgtctatat                                                    19

<210> SEQ ID NO 5
<211> LENGTH: 19
<212> TYPE: DNA
<213> ORGANISM: Artificial Sequence
<220> FEATURE:

<223> OTHER INFORMATION: Synthetic oligonucleotide

<400> SEQUENCE: 5
agacttagct ccctgaaat                                                19

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
cgtgtagtgc agccaaatt                                                19

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
tcgtcttcgt cgtacaagt                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 8
atatgtcctc ctgggaaga                                                19

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
gccggaacag ctcaagttt                                                19

<210> SEQ ID NO 10
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 10
tttctatctg tttaaagga                                                19

<210> SEQ ID NO 11
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 11
ccatataacc catggtaga                                                19

```
<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
gcttcaaacg tgtgtgaat                                                  19

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
agccgtttct aaacttaat                                                  19

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 14
ctgaaatacg ttggatagt                                                  19

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 15
gttggatagt cgttctgtt                                                  19

<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
tgccttagcc ttgtctata                                                  19

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 17
ctagccgttt ctaaactta                                                  19

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide
```

<400> SEQUENCE: 18
gcaagctgtg actatagaa                                               19

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
gtgttaagtt tgtgtctca                                               19

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 20
tgctagaagt gttaagttt                                               19

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
cagccacgtt ctttaaatt                                               19

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
aagtttgtgt ctcaatact                                               19

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
agagcaagat tagaataaa                                               19

<210> SEQ ID NO 24
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 24
tgcattacag aatggtaat                                               19

<210> SEQ ID NO 25
<211> LENGTH: 19

```
<212> TYPE: RNA
<213> ORGANISM: Artificial Sequence
<220> FEATURE:
<223> OTHER INFORMATION: Synthetic oligonucleotide

<400> SEQUENCE: 25
gacuuagcuc ccugaaaua                                                    19

<210> SEQ ID NO 26
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 26
gccuuagccu ugucuauau                                                    19

<210> SEQ ID NO 27
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 27
agacuuagcu cccugaaau                                                    19

<210> SEQ ID NO 28
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 28
cguguagugc agccaaauu                                                    19

<210> SEQ ID NO 29
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 29
ucgucuucgu cguacaagu                                                    19

<210> SEQ ID NO 30
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 30
auauguccuc cugggaaga                                                    19

<210> SEQ ID NO 31
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 31
```
gccggaacag cucaaguuu                                                    19

<210> SEQ ID NO 32
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 32
uuucuaucug uuuaaagga                                                    19

<210> SEQ ID NO 33
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 33
ccauauaacc caugguaga                                                    19

<210> SEQ ID NO 34
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 34
gcuucaaacg ugugugaau                                                    19

<210> SEQ ID NO 35
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 35
agccguuucu aaacuuaau                                                    19

<210> SEQ ID NO 36
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 36
cugaaauacg uuggauagu                                                    19

<210> SEQ ID NO 37
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 37
guuggauagu cguucuguu                                                    19

<210> SEQ ID NO 38
<211> LENGTH: 19
<212> TYPE: RNA
<213> ORGANISM: Artificial Sequence

```
<220> FEATURE:
<223> OTHER INFORMATION: Synthetic oligonucleotide

<400> SEQUENCE: 38
ugccuuagcc uugucuaua                                                    19

<210> SEQ ID NO 39
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 39
cuagccguuu cuaaacuua                                                    19

<210> SEQ ID NO 40
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 40
gcaagcugug acuauagaa                                                    19

<210> SEQ ID NO 41
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 41
guguuaaguu ugugucuca                                                    19

<210> SEQ ID NO 42
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 42
ugcuagaagu guuaaguuu                                                    19

<210> SEQ ID NO 43
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 43
cagccacguu cuuuaaauu                                                    19

<210> SEQ ID NO 44
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 44 aaguugugu cucaauacu                                                     19
```

```
<210> SEQ ID NO 45
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 45
agagcaagau uagaauaaa                                                       19

<210> SEQ ID NO 46
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 46
ugcauuacag aaugguaau                                                       19

<210> SEQ ID NO 47
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 47
uauuucaggg agcuaaguc                                                       19

<210> SEQ ID NO 48
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 48
auauagacaa ggcuaaggc                                                       19

<210> SEQ ID NO 49
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 49
auuucaggga gcuaagucu                                                       19

<210> SEQ ID NO 50
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 50
aauuuggcug cacuacacg                                                       19

<210> SEQ ID NO 51
<211> LENGTH: 19
<212> TYPE: RNA
<213> ORGANISM: Artificial Sequence
<220> FEATURE:
<223> OTHER INFORMATION: Synthetic oligonucleotide
```

<400> SEQUENCE: 51
acuuguacga cgaagacga                                          19

<210> SEQ ID NO 52
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 52
ucuucccagg aggacauau                                          19

<210> SEQ ID NO 53
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 53
aaacuugagc uguuccggc                                          19

<210> SEQ ID NO 54
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 54
uccuuuaaac agauagaaa                                          19

<210> SEQ ID NO 55
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 55
ucuaccaugg guuauaugg                                          19

<210> SEQ ID NO 56
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 56
auucacacac guuugaagc                                          19

<210> SEQ ID NO 57
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 57
auuaaguuua gaaacggcu                                          19

<210> SEQ ID NO 58

```
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 58
acuauccaac guauuucag                                                    19

<210> SEQ ID NO 59
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 59
aacagaacga cuauccaac                                                    19

<210> SEQ ID NO 60
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 60
uauagacaag gcuaaggca                                                    19

<210> SEQ ID NO 61
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 61
uaaguuuaga aacggcuag                                                    19

<210> SEQ ID NO 62
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 62
uucuauaguc acagcuugc                                                    19

<210> SEQ ID NO 63
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 63
ugagacacaa acuuaacac                                                    19

<210> SEQ ID NO 64
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 64
```

```
aaacuuaaca cuucuagca                                        19

<210> SEQ ID NO 65
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 65
aauuuaaaga acguggcug                                        19

<210> SEQ ID NO 66
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 66
aguauugaga cacaaacuu                                        19

<210> SEQ ID NO 67
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 67
uuuauucuaa ucuugcucu                                        19

<210> SEQ ID NO 68
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 68
auuaccauuc uguaaugca                                        19

<210> SEQ ID NO 69
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 69
gacuuagcuc ccugaaauau u                                     21

<210> SEQ ID NO 70
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 70
gccuuagccu ugucuauauu u                                     21

<210> SEQ ID NO 71
<211> LENGTH: 21
<212> TYPE: RNA
```

```
<213> ORGANISM: Artificial Sequence
<220> FEATURE:
<223> OTHER INFORMATION: Synthetic oligonucleotide

<400> SEQUENCE: 71
agacuuagcu cccugaaauu u                                              21

<210> SEQ ID NO 72
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 72
cguguagugc agccaaauuu u                                              21

<210> SEQ ID NO 73
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 73
ucgucuucgu cguacaaguu u                                              21

<210> SEQ ID NO 74
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 74
auauguccuc cugggaagau u                                              21

<210> SEQ ID NO 75
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 75
gccggaacag cucaaguuuu u                                              21

<210> SEQ ID NO 76
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 76
uuucuaucug uuuaaaggau u                                              21
```

```
<210> SEQ ID NO 77
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 77
ccauauaacc caugguagau u                                              21

<210> SEQ ID NO 78
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 78
gcuucaaacg ugugugaauu u                                              21

<210> SEQ ID NO 79
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 79
agccguuucu aaacuuaauu u                                              21

<210> SEQ ID NO 80
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 80
cugaaauacg uuggauaguu u                                              21

<210> SEQ ID NO 81
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 81
guuggauagu cguucuguuu u                                              21

<210> SEQ ID NO 82
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 82
ugccuuagcc uugucuauau u                                              21

<210> SEQ ID NO 83
```

```
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 83
cuagccguuu cuaaacuuau u                                              21

<210> SEQ ID NO 84
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 84
gcaagcugug acuauagaau u                                              21

<210> SEQ ID NO 85
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 85
guguuaaguu ugugucucau u                                              21

<210> SEQ ID NO 86
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 86
ugcuagaagu guuaaguuuu u                                              21

<210> SEQ ID NO 87
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 87
cagccacguu cuuuaaauuu u                                              21

<210> SEQ ID NO 88
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 88 aaguugugu cucaauacuu u                                               21

<210> SEQ ID NO 89
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 89
```
agagcaagau uagaauaaau u                                              21

<210> SEQ ID NO 90
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 90
ugcauuacag aaugguaauu u                                              21

<210> SEQ ID NO 91
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 91
uauuucaggg agcuaagucu u                                              21

<210> SEQ ID NO 92
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 92
auauagacaa ggcuaaggcu u                                              21

<210> SEQ ID NO 93
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 93
auuucaggga gcuaagucuu u                                              21

<210> SEQ ID NO 94
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 94
aauuuggcug cacuacacgu u                                              21

<210> SEQ ID NO 95
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 95
acuuguacga cgaagacgau u                                              21

<210> SEQ ID NO 96
<211> LENGTH: 21
<212> TYPE: RNA

```
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 96
ucuucccagg aggacauauu u                                              21

<210> SEQ ID NO 97
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 97
aaacuugagc uguuccggcu u                                              21

<210> SEQ ID NO 98
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 98
uccuuuaaac agauagaaau u                                              21

<210> SEQ ID NO 99
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: 2'-OMe modified nucleotide

<400> SEQUENCE: 99
ucuaccaugg guuauauggu u                                              21

<210> SEQ ID NO 100
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 100
auucacacac guuugaagcu u                                              21

<210> SEQ ID NO 101
<211> LENGTH: 21
<212> TYPE: RNA
<213> ORGANISM: Artificial Sequence
<220> FEATURE:
<223> OTHER INFORMATION: Synthetic oligonucleotide
```

<400> SEQUENCE: 101
auuaaguuua gaaacggcuu u                                              21

<210> SEQ ID NO 102
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 102
acuauccaac guauuucagu u                                              21

<210> SEQ ID NO 103
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 103
aacagaacga cuauccaacu u                                              21

<210> SEQ ID NO 104
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 104
uauagacaag gcuaaggcau u                                              21

<210> SEQ ID NO 105
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 105
uaaguuuaga aacggcuagu u                                              21

<210> SEQ ID NO 106
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 106
uucuauaguc acagcuugcu u                                              21

<210> SEQ ID NO 107
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 107
ugagacacaa acuuaacacu u                                              21

<210> SEQ ID NO 108

```
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 108
aaacuuaaca cuucuagcau u                                              21

<210> SEQ ID NO 109
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 109
aauuuaaaga acguggcugu u                                              21

<210> SEQ ID NO 110
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 110
aguauugaga cacaaacuuu u                                              21

<210> SEQ ID NO 111
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 111
uuuauucuaa ucuugcucuu u                                              21

<210> SEQ ID NO 112
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 112
auuaccauuc uguaaugcau u                                              21
```

SIRT1-SARNA COMPOSITIONS AND METHODS OF USE

CROSS REFERENCE TO RELATED APPLICATIONS

This application is a 35 U.S.C. § 371 U.S. National Stage Entry of International Application No. PCT/GB2019/051061 filed Apr. 12, 2019, which claims the benefit of priority to U.S. Provisional Application No. 62/656,465, filed Apr. 12, 2018, entitled SIRT1-SARNA COMPOSITIONS AND METHODS OF USE, the contents of which are incorporated herein by reference in its entirety.

REFERENCE TO SEQUENCE LISTING

The present application is being filed along with a Sequence Listing in electronic format. The sequence listing filed, entitled 20581023US371_SEQLIST, was created on Oct. 9, 2020 and is 33,496 bytes in size. The information in electronic format of the Sequence Listing is incorporated herein by reference in its entirety.

FIELD OF THE INVENTION

The invention relates to oligonucleotide, specifically saRNA, compositions for modulating SIRT1 (Sirtuin 1) gene expression and to the methods of using the compositions in diagnostic and therapeutic applications.

BACKGROUND OF THE INVENTION

Recently it has been discovered that small duplex RNAs increased gene expression by targeting ncRNAs that overlap gene promoters (Janowski et al., *Nature Chemical Biology*, vol. 3:166-173 (2007), the contents of which are incorporated herein by reference in their entirety). Any short RNA which leads to up-regulation of the expression of a target gene by any mechanism is termed a short activating RNA or small activating RNA (saRNA). Known methods of up-regulating a target gene by use of saRNAs can involve the detection of an RNA transcript which is antisense to the target gene of interest and designing short RNA molecules which down-regulate the identified transcript. For instance, U.S. Pat. No. 8,288,354 to Wahlestedt, the contents of which are incorporated herein by reference in their entirety, discloses a method of modulating expression of a target gene comprising targeting a nucleic acid molecule to a naturally-occurring anti-sense transcript (NAT) of a sense strand of the targeted gene in a target cell, wherein the nucleic acid molecule targeting the NAT is complementary to the NAT. The NAT may be a coding RNA transcript or a non-coding RNA transcript lacking any extensive open reading frame. In another example, WO 2012/065143 to Krieg et al., the contents of which are incorporated herein by reference in their entirety, teaches a method of activating expression of a target gene comprising blocking the binding of a long non-coding RNA (lnc-RNA) to Polycomb repressive complex 2 (PRC2) protein by a single-stranded oligonucleotide, thereby preventing the lnc-RNA from suppressing the target gene.

There remains, however, a need for compositions and methods for the targeted modulation of genes via activation with saRNA which do not require the a priori identification of a NAT or rely on interactions at the polycomb complex for prophylactic diagnostic and/or therapeutic purposes.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 1 is a schematic illustrating the relationships among the nucleic acid moieties involved in the function of a saRNA of the invention.

SUMMARY OF THE INVENTION

The present invention provides compositions, methods and kits for the design, preparation, manufacture, formulation and/or use of short activating RNA (saRNA) molecules that modulate SIRT1 gene expression and/or function for therapeutic purposes, including diagnosing and prognosis.

One aspect of the invention provides a pharmaceutical composition comprising a saRNA that targets a SIRT1 transcript and at least one pharmaceutically acceptable carrier.

Yet another aspect of the invention provides a method of regulating stem cell differentiation and pluripotency comprising contact said stem cell with a saRNA that targets a SIRT1 transcript.

The details of various embodiments of the invention are set forth in the description below. Other features, objects, and advantages of the invention will be apparent from the description and the drawings, and from the claims.

DETAILED DESCRIPTION

The present invention provides compositions, methods and kits for modulating SIRT1 gene expression and/or function for therapeutic purposes. These compositions, methods and kits comprise at least one saRNA that upregulates the expression of the SIRT1 gene.

SIRT1 protein encoded by the SIRT1 gene is an enzyme that deacetylates proteins that contribute to cellular regulation and is involved Longevity regulating pathway and E2F transcription factor network. Modulating SIRT1 gene has great potentials for therapeutic purposes. The present invention addresses this need by providing nucleic acid constructs targeting a SIRT1 transcript, wherein the nucleic acid constructs may include single or double stranded DNA or RNA with or without modifications.

SIRT1 gene as used herein is a double-stranded DNA comprising a coding strand and a template strand. The template strand has a promotor region. The "coding strand" of a gene has the same base sequence as the mRNA produced, except T is replayed by U in the mRNA. The "template strand" of a gene is therefore complementary and antiparallel to the mRNA produced.

The terms "SIRT1 transcript", "SIRT1 target transcript" or "target transcript" in the context may be SIRT1 mRNA encoding SIRT1 protein. SIRT1 mRNA is transcribed from the template strand of SIRT1 gene and may exist in the mitochondria.

I. Design and Synthesis of saRNA

One aspect of the present invention provides a method to design and synthesize saRNA.

The terms "small activating RNA", "short activating RNA", or "saRNA" in the context of the present invention means a single-stranded or double-stranded RNA that upregulates or has a positive effect on the expression of a specific gene. The saRNA may be single-stranded of 14 to 30 nucleotides. The saRNA may also be double-stranded, each strand comprising 14 to 30 nucleotides. The gene is called the target gene of the saRNA. As used herein, the target gene is the SIRT1 gene. For example, a saRNA that upregulates the expression of the SIRT1 gene is called an "SIRT1-saRNA" and the SIRT1 gene is the target gene of the SIRT1-saRNA.

By "upregulation" or "activation" of a gene is meant an increase in the level of expression of a gene, or levels of the polypeptide(s) encoded by a gene or the activity thereof, or levels of the RNA transcript(s) transcribed from the template strand of a gene above that observed in the absence of the saRNA of the present invention. The saRNA of the present invention may have a direct upregulating effect on the expression of the target gene.

The saRNAs of the present invention may have an indirect upregulating effect on the RNA transcript(s) transcribed from the template strand of the target gene and/or the polypeptide(s) encoded by the target gene or mRNA. The RNA transcript transcribed from the target gene is referred to thereafter as the target transcript. The target transcript may be an mRNA of the target gene. The target transcript may exist in the mitochondria. The saRNAs of the present invention may have a downstream effect on a biological process or activity. In such embodiments, a saRNA targeting a first transcript may have an effect (either upregulating or downregulating) on a second, non-target transcript.

Targeted Sequence

In some embodiments, the saRNA comprises an antisense strand that is at least 80% complementary to a region on the template strand of the target gene. This region on the template strand, where the strand of the saRNA hybridizes or binds to, is referred to as the "targeted sequence" or "target site". FIG. 1 illustrates the relationships between the antisense strand and the targeted region on the template strand.

The term "complementary to" in the context means being able to hybridize under stringent conditions. It is to be understood that thymidine of the DNA is replaced by uridine in RNA and that this difference does not alter the understanding of the term "complementarity".

The antisense strand of the saRNA (whether single- or double-stranded) may be at least 80%, 90%, 95%, 98%, 99% or 100% identical with the reverse complement of the targeted sequence. Thus, the reverse complement of the antisense strand of the saRNA has a high degree of sequence identity with the targeted sequence. The targeted sequence may have the same length, i.e., the same number of nucleotides, as the saRNA and/or the reverse complement of the saRNA.

In some embodiments, the targeted sequence comprises at least 14 and less than 30 nucleotides.

In some embodiments, the targeted sequence has 19, 20, 21, 22, or 23 nucleotides.

In some embodiments, the location of the targeted sequence is situated within a promoter area of the template strand.

In some embodiments, the targeted sequence is located within a TSS (transcription start site) core of the template stand. A "TSS core" or "TSS core sequence" as used herein, refers to a region between 2000 nucleotides upstream and 2000 nucleotides downstream of the TSS (transcription start site). Therefore, the TSS core comprises 4001 nucleotides and the TSS is located at position 2001 from the 5' end of the TSS core sequence. The term "transcription start site" (TSS) as used herein means a nucleotide on the template strand of a gene corresponding to or marking the location of the start of transcription. The TSS may be located within the promoter region on the template strand of the gene.

In some embodiments, the targeted sequence is located between 1000 nucleotides upstream and 1000 nucleotides downstream of the TSS.

In some embodiments, the targeted sequence is located between 500 nucleotides upstream and 500 nucleotides downstream of the TSS.

In some embodiments, the targeted sequence is located between 250 nucleotides upstream and 250 nucleotides downstream of the TSS.

In some embodiments, the targeted sequence is located between 100 nucleotides upstream and 100 nucleotides downstream of the TSS.

In some embodiments, the targeted sequence is located upstream of the TSS in the TSS core. The targeted sequence may be less than 2000, less than 1000, less than 500, less than 250, or less than 100 nucleotides upstream of the TSS.

In some embodiments, the targeted sequence is located downstream of the TSS in the TSS core. The targeted sequence may be less than 2000, less than 1000, less than 500, less than 250, or less than 100 nucleotides downstream of the TSS.

In some embodiments, the targeted sequence is located +/−50 nucleotides surrounding the TSS of the TSS core. In some embodiments, the targeted sequence substantially overlaps the TSS of the TSS core. In some embodiments, the targeted sequence begins or ends at the TSS of the TSS core. In some embodiments, the targeted sequence overlaps the TSS of the TSS core by 1, 2, 3, 4, 5, 6, 7, 8, 9, 10, 11, 12, 13, 14, 15, 16, 17, 18 or 19 nucleotides in either the upstream or downstream direction.

The location of the targeted sequence on the template strand is defined by the location of the 5' end of the targeted sequence. The 5' end of the targeted sequence may be at any position of the TSS core and the targeted sequence may start at any position selected from position 1 to position 4001 of the TSS core. For reference herein, when the 5' end of the targeted sequence from position 1 to position 2000 of the TSS core, the targeted sequence is considered upstream of the TSS and when the 5' end of the targeted sequence is from position 2002 to 4001, the targeted sequence is considered downstream of the TSS. When the 5' end of the targeted sequence is at nucleotide 2001, the targeted sequence is considered to be a TSS centric sequence and is neither upstream nor downstream of the TSS.

For further reference, for example, when the 5' end of the targeted sequence is at position 1600 of the TSS core, i.e., it is the $1600^{th}$ nucleotide of the TSS core, the targeted sequence starts at position 1600 of the TSS core and is considered to be upstream of the TSS.

saRNA

In one embodiment, the saRNA of the present invention is a single-stranded saRNA. The single-stranded saRNA may be at least 14, or at least 18, e.g. 19, 20, 21 or 22 nucleotides in length. Preferably, the length of the single-stranded saRNA is less than 30 nucleotides. In some embodiments, the length of the single-stranded saRNA is 19 to 25 nucleotides. In one embodiment, the single-stranded saRNA may be exactly 19 nucleotides in length. In another embodiment, the single-stranded saRNA may be exactly 20 nucleotides in length. In yet another embodiment, the single-stranded saRNA may be exactly 21 nucleotides in length. In some embodiments, the single-stranded saRNA of the present invention comprises a sequence of at least 14 nucleotides and less than 30 nucleotides, which has at least 80%, 90%, 95%, 98%, 99% or 100% complementarity to the targeted sequence. In one embodiment, the sequence which has at least 80%, 90%, 95%, 98%, 99% or 100% complementarity to the targeted sequence is at least 15, 16, 17, 18 or 19 nucleotides in length, or 18 to 22, or 19 to 21, or exactly 19.

In another embodiment, the saRNA of the present invention has two strands that form a duplex, one strand being an antisense or guide strand. The saRNA duplex is also called a double-stranded saRNA. A double-stranded saRNA or saRNA duplex, as used herein, is a saRNA that includes more than one, and preferably, two, strands in which inter-strand hybridization can form a region of duplex structure.

The two strands of a double-stranded saRNA are referred to as an antisense strand or a guide strand, and a sense strand or a passenger strand.

Each strand of the duplex may be at least 14, or at least 18, e.g. 19, 20, 21 or 22 nucleotides in length. The duplex may be hybridized over a length of at least 12, or at least 15, or at least 17, or at least 19 nucleotides. Each strand may be exactly 19, 20, or 21 nucleotides in length. Preferably, the length of each strand of the saRNA is less than 30 nucleotides since oligonucleotide duplex exceeding this length may have an increased risk of inducing the interferon response. In one embodiment, the length of each strand of the saRNA is 19 to 25 nucleotides. The strands forming the saRNA duplex may be of equal or unequal lengths.

In one embodiment, the antisense strand of the saRNA of the present invention comprises a sequence of at least 14 nucleotides and less than 30 nucleotides which has at least 80%, 90%, 95%, 98%, 99% or 100% complementarity to the targeted sequence. In one embodiment, the sequence which has at least 80%, 90%, 95%, 98%, 99% or 100% complementarity to the targeted sequence is at least 15, 16, 17, 18 or 19 nucleotides in length, or 18 to 22, or 19 to 21, or exactly 19.

The antisense strand may have no more than 5, or no more than 4 or 3, or no more than 2, or no more than 1, or no mismatches with the targeted sequence on the template strand. Therefore, the antisense strand has a high degree of complementarity to the targeted sequence on the template strand. The sense strand of the saRNA duplex has a high degree of sequence identity with the targeted sequence on the template strand.

The relationships among the saRNA duplex, a target gene, a coding strand of the target gene, a template strand of the target gene, a target transcript, a targeted sequence/target site, and the TSS are shown in FIG. 1.

A "strand" in the context of the present invention means a contiguous sequence of nucleotides, including non-naturally occurring or modified nucleotides. Two or more strands may be, or each form a part of, separate molecules, or they may be connected covalently, e.g., by a linker such as a polyethyleneglycol linker. At least one strand of a saRNA may comprise a region that is complementary to a target antisense RNA. Such a strand is called an antisense or guide strand of the saRNA duplex. A second strand of a saRNA that comprises a region complementary to the antisense strand of the saRNA is called a sense or passenger strand.

A saRNA duplex may also be formed from a single molecule that is at least partly self-complementary forming a hairpin structure, including a duplex region. In such case, the term "strand" refers to one of the regions of the saRNA that is complementary to another internal region of the saRNA. The guide strand of the saRNA will have no more than 5, or no more than 4 or 3, or no more than 2, or no more than 1, or no mismatches with the sequence within the target antisense RNA transcript.

In some embodiments, the passenger strand of a saRNA may comprise at least one nucleotide that is not complementary to the corresponding nucleotide on the guide strand, called a mismatch with the guide strand. The mismatch with the guide strand may encourage preferential loading of the guide strand (Wu et al., *PLoS ONE*, vol. 6 (12):e28580 (2011), the contents of which are incorporated herein by reference in their entirety). In one embodiment, the at least one mismatch with the guide strand may be at 3' end of the passenger strand. In one embodiment, the 3' end of the passenger strand may comprise 1-5 mismatches with the guide strand. In one embodiment, the 3' end of the passenger strand may comprise 2-3 mismatches with the guide strand. In one embodiment, the 3' end of the passenger strand may comprise 6-10 mismatches with the guide strand.

A saRNA duplex may have siRNA-like complementarity to the targeted sequence on the template strand; that is, 100% complementarity between nucleotides 2-6 from the 5' end of the guide strand in the saRNA duplex and a region on the targeted sequence. Other nucleotides of the saRNA may, in addition, have at least 80%, 90%, 95%, 98%, 99% or 100% complementarity to a region of the targeted sequence. For example, nucleotides 7 (counted from the 5' end) until the 3' end of the saRNA may have least 80%, 90%, 95%, 98%, 99% or 100% complementarity to a region of the targeted sequence.

The terms "small interfering RNA" or "siRNA" in the context mean a double-stranded RNA typically 20-25 nucleotides long involved in the RNA interference (RNAi) pathway and interfering with or inhibiting the expression of a specific gene. The gene is the target gene of the siRNA. A siRNA is usually about 21 nucleotides long, with 3' overhangs (e.g., 2 nucleotides) at each end of the two strands.

A siRNA inhibits target gene expression by binding to and promoting the cleavage of one or more RNA transcripts of the target gene at specific sequences. Typically, in RNAi the RNA transcripts are mRNA, so cleavage of mRNA results in the down-regulation of gene expression. In the present invention, not willing to be bound with any theory, one of the possible mechanisms is that saRNA of the present invention may modulate the target gene expression by cleavage of a target antisense RNA transcript, which maybe a natural antisense transcript (NAT) of the target gene. As illustrated in FIG. 1, the target antisense RNA transcript is complementary to the coding strand of the target gene. However, the existence of the target antisense RNA transcript does not need to be identified. In some embodiments, the target antisense RNA transcript may not be cleaved or down-regulated by the saRNA of the present invention.

In some embodiments, the saRNA may comprise a number of unpaired nucleotides at the 3' end of each strand forming 3' overhangs or tails. The number of unpaired nucleotides forming the 3' overhang of each strand may be in the range of 1 to 5 nucleotides, or 1 to 3 nucleotides, or 2 nucleotides.

Thus, in some embodiments, the saRNA of the present invention may be single-stranded and consists of (i) a sequence having at least 80% complementarity to a targeted sequence on the template strand of the target gene; and (ii) a 3' tail of 1-5 nucleotides, which may comprise uracil residues, such as UU, UUU, or mUmU (m strands for 2'-OMe modification). In some embodiments, the saRNA of the present invention may be double-stranded and consists of a first strand comprising (i) a first sequence having at least 80% complementarity to a targeted sequence on the template strand of the target gene; and (ii) a 3' overhang of 1-5 nucleotides; and a second strand comprising (i) a second sequence that forms a duplex with the first sequence and (ii) a 3' overhang of 1-5 nucleotides. Such a 3' tail shall not be regarded as mismatches with regard to determine complementarity between the saRNA antisense strand and the targeted sequence. The saRNA of the present invention may have complementarity to the targeted sequence over its whole length, except for the 3' tail, if present.

The saRNA of the present invention may contain a flanking sequence. The flanking sequence may be inserted in the 3' end or 5' end of the saRNA of the present invention. In one embodiment, the flanking sequence is the sequence of a miRNA, rendering the saRNA to have miRNA configuration and may be processed with Drosha and Dicer. In a non-limiting example, the saRNA of the present invention has two strands and is cloned into a microRNA precursor, e.g., miR-30 backbone flanking sequence.

The saRNA of the present invention may comprise a restriction enzyme substrate or recognition sequence. The restriction enzyme recognition sequence may be at the 3' end or 5' end of the saRNA of the present invention. Non-limiting examples of restriction enzymes include NotI and AscI.

SIRT1 Gene and SIRT1-saRNAs

As discussed above, the antisense strand of the saRNA has a high degree of sequence identity with the reverse complement of the targeted sequence. Instead of "complementary to the targeted sequence," the antisense strand of the saRNA of the present invention may also be defined as having "identity" to a region on the coding strand of the target gene. Therefore, the genomic sequence of the target gene may be used to design saRNAs.

Sequences of SIRT1 gene, SIRT1 protein, SIRT1-mRNA, and SIRT1 TSS cores are provided in Table 1.

TABLE 1

Sequences of SIRT1 Gene and SIRT1 Protein

| Target Gene | Nature of gene | Location on chromosome | Protein encoded by the target gene | mRNA transcribed from the target gene (target transcript) | Location on the coding strand that corresponds to the target transcript's TSS | SEQ ID of TSS core |
|---|---|---|---|---|---|---|
| SIRT1 human | Coding | 10q21.3 | NP_001135970 | NM_001142498 | chr10: 67885180 plus strand | 1 |
|  |  |  | NP_036370 | NM_012238 | chr10: 67884668 plus strand | 2 |

The saRNA antisense strand sequence's off-target hit number in the whole genome, 0 mismatch (0 mm) hit number, and 1 mismatch (1 mm) hit number are then determined. The term "off-target hit number" refers to the number of other sites in the whole genome that are identical to the saRNA's targeted sequence on the template strand of the target gene. The term "0 mm hit number" refers to the number of known protein coding transcript other than the target transcript of the saRNA, the complement of which the saRNA may hybridize with or bind to with 0 mismatch. In another word, "0 mm hit number" counts the number of known protein coding transcript, other than the target transcript of the saRNA that comprises a region completely identical with the saRNA antisense strand sequence. The term "1 mm hit number" refers to the number of known protein coding transcript other than the target transcript of the saRNA, the complement of which the saRNA may hybridize with or bind to with 1 mismatch. In another word, "1 mm hit number" counts the number of known protein coding transcript, other than the target transcript of the saRNA that comprises a region identical with the saRNA antisense strand sequence with only 1 mismatch. In one embodiment, only saRNA antisense strand sequences that have no off-target hit defined as no 0 mm hit and no 1 mm hit are selected. For those saRNA sequences disclosed in the present application, each has no off-target hit define as no 0 mm hit and no 1 mm hit.

Table 2 describes the SIRT1-saRNAs' targeted sequences, the genomic location of the targeted sequences, and the relative location of SIRT1-saRNAs with no 3' overhang. In Table 2, the targeted sequence is defined as a region on the template strand of the SIRT1 gene. The relative location is the distance from the 5' end of the targeted sequence to the TSS. A negative number represents a location upstream of the TSS and a positive number represents a location downstream of the TSS. "SIRT1-Tr-NM_012238-Pr-57-Cp-0" in Table 2 and Table 4 is also referred to as PR57 or PR-57 in the current application.

TABLE 2

Targeted Sequences of SIRT1-saRNAs

| saRNA ID | Target gene | Targeted sequence | Targeted sequence SEQ ID No. | hg38 genomic location of the targeted sequence | Relative location to TSS (TSS = 0) |
|---|---|---|---|---|---|
| SIRT1-Pr-1 | SIRT1 human NM_012238 | gacttagctcc ctgaaata | 3 | chr10: 67884228 minus strand | 422 |

TABLE 2-continued

Targeted Sequences of SIRT1-saRNAs

| saRNA ID | Target gene | Targeted sequence | Targeted sequence SEQ ID No. | hg38 genomic location of the targeted sequence | Relative location to TSS (TSS = 0) |
|---|---|---|---|---|---|
| SIRT1-Pr-2 | SIRT1 human NM_012238 | gccttagcctt gtctatat | 4 | chr10: 67884283 minus strand | 367 |
| SIRT1-Pr-3 | SIRT1 human NM_012238 | agacttagctc cctgaaat | 5 | chr10: 67884229 minus strand | 421 |
| SIRT1-Pr-4 | SIRT1 human NM_012238 | cgtgtagtgc agccaaatt | 6 | chr10: 67884424 minus strand | 226 |
| SIRT1-Pr-5 | SIRT1 human NM_012238 | tcgtcttcgtc gtacaagt | 7 | chr10: 67885077 minus strand | −427 |
| SIRT1-Tr-NM_012238-Pr-57-Cp-0 | SIRT1 human NM_012238 | atatgtcctcct gggaaga | 8 | chr10: 67884009 minus strand | 641 |
| SIRT1-Tr-NM_012238-Pr-232-Cp-0 | SIRT1 human NM_012238 | gccggaaca gctcaagttt | 9 | chr10: 67884351 minus strand | 299 |
| SIRT1-Tr-NM_012238-Pr-89-Cp-0 | SIRT1 human NM_012238 | tttctatctgttt aaagga | 10 | chr10: 67883514 minus strand | 1136 |
| SIRT1-Tr-NM_012238-Pr-87-Cp-0 | SIRT1 human NM_012238 | ccatataaccc atggtaga | 11 | chr10: 67883576 minus strand | 1074 |
| SIRT1.NM_012238-Pr-6 | SIRT1 human NM_012238 | gcttcaaacgt gtgtgaat | 12 | chr10: 67883937 minus strand | 713 |
| SIRT1.NM_012238-Pr-17 | SIRT1 human NM_012238 | agccgtttcta aacttaat | 13 | chr10: 67883774 minus strand | 876 |
| SIRT1.NM_012238-Pr-19 | SIRT1 human NM_012238 | ctgaaatacgt tggatagt | 14 | chr10: 67884217 minus strand | 433 |
| SIRT1.NM_012238-Pr-30 | SIRT1 human NM_012238 | gttggatagtc gttctgtt | 15 | chr10: 67884208 minus strand | 442 |
| SIRT1.NM_012238-Pr-38 | SIRT1 human NM_012238 | tgccttagcct tgtctata | 16 | chr10: 67884284 minus strand | 366 |
| SIRT1.NM_012238-Pr-39 | SIRT1 human NM_012238 | ctagccgtttc taaactta | 17 | chr10: 67883776 minus strand | 874 |
| SIRT1.NM_001142498-Pr-1 | SIRT1 human NM_001142498 | gacttagctcc ctgaaata | 3 | chr10: 67884228 minus strand | 934 |
| SIRT1.NM_001142498-Pr-2 | SIRT1 human NM_001142498 | agacttagctc cctgaaat | 5 | chr10: 67884229 minus strand | 933 |
| SIRT1.NM_001142498-Pr-13 | SIRT1 human NM_001142498 | gcaagctgtg actatagaa | 18 | chr10: 67885677 minus strand | −515 |
| SIRT1.NM_001142498-Pr-18 | SIRT1 human NM_001142498 | gtgttaagtttg tgtctca | 19 | chr10: 67885870 minus strand | −708 |
| SIRT1.NM_001142498-Pr-19 | SIRT1 human NM_001142498 | gccttagcctt gtctatat | 4 | chr10: 67884283 minus strand | 879 |
| SIRT1.NM_001142498-Pr-23 | SIRT1 human NM_001142498 | tgctagaagt gttaagttt | 20 | chr10: 67885878 minus strand | −716 |
| SIRT1.NM_001142498-Pr-24 | SIRT1 human NM_001142498 | cagccacgtt ctttaaatt | 21 | chr10: 67885698 minus strand | −536 |
| SIRT1.NM_001142498-Pr-25 | SIRT1 human NM_001142498 | ctgaaatacgt tggatagt | 14 | chr10: 67884217 minus strand | 945 |
| SIRT1.NM_001142498-Pr-26 | SIRT1 human NM_001142498 | aagtttgtgtct caatact | 22 | chr10: 67885865 minus strand | −703 |
| SIRT1.NM_001142498-Pr-34 | SIRT1 human NM_001142498 | gttggatagtc gttctgtt | 15 | chr10: 67884208 minus strand | 954 |
| SIRT1.NM_001142498-Pr-36 | SIRT1 human NM_001142498 | agagcaagat tagaataaa | 23 | chr10: 67885798 minus strand | −636 |
| SIRT1.NM_001142498-Pr-37 | SIRT1 human NM_001142498 | tgcattacaga atggtaat | 24 | chr10: 67885728 minus strand | −566 |

SIRT1-saRNAs may be single-stranded and comprise 14-30 nucleotides. The sequence of a single-stranded SIRT1-saRNA may have at least 60%, 70%, 80% or 90% identity with a sequence selected from the sequences of the antisense strands in Table 3. In one embodiment, the single-stranded saRNA comprises a sequence selected from the sequences of the antisense strands in Table 3. In one embodiment, the single-stranded SIRT1-saRNA may have a 3' tail. The sequence of a single-stranded SIRT1-saRNA with a 3' tail may have at least 60%, 70%, 80% or 90% identity with a sequence selected from the sequences of the antisense strands in Table 4. In one embodiment, the single-stranded saRNA comprises a sequence selected from the sequences of the antisense strands in Table 4.

SIRT1-saRNAs may be double-stranded. The two strands form a duplex and each strand comprises 14-30 nucleotides. The first strand of a double-stranded SIRT1-saRNA may have at least 60%, 70%, 80% or 90% identity with a sequence selected from the sequences of the antisense strands in Table 3. In one embodiment, the first strand of the double-stranded saRNA comprises a sequence selected from the sequences of the antisense strands in Table 3. The second strand of a double-stranded SIRT1-saRNA may have at least 60%, 70%, 80% or 90% identity with a sequence selected from the sequences of the sense strands in Table 3. In one embodiment, the second strand of the double-stranded saRNA comprises a sequence selected from the sequences of the sense strands in Table 3. In one embodiment, the double-stranded SIRT1-saRNA may have a 3' overhang on each strand. The first strand of a double-stranded SIRT1-saRNA may have at least 60%, 70%, 80% or 90% identity with a sequence selected from the sequences of the antisense strands in Table 4. In one embodiment, the first strand of the double-stranded saRNA comprises a sequence selected from the sequences of the antisense strands in Table 4. The second strand of a double-stranded SIRT1-saRNA may have at least 60%, 70%, 80% or 90% identity with a sequence selected from the sequences of the sense strands in Table 4. In one embodiment, the second strand of the double-stranded saRNA comprises a sequence selected from the sequences of the sense strands in Table 4.

SIRT1-saRNAs may be modified or unmodified.

TABLE 3

Sequences of SIRT1-saRNAs (with no 3' overhang)

| saRNA ID | Sense sequence | SEQ ID No. | Antisense sequence | SEQ ID No. |
| --- | --- | --- | --- | --- |
| SIRT1-Pr-1' | GACUUAGCUCCCUGAAAUA | 25 | UAUUUCAGGGAGCUAAGUC | 47 |
| SIRT1-Pr-2' | GCCUUAGCCUUGUCUAUAU | 26 | AUAUAGACAAGGCUAAGGC | 48 |
| SIRT1-Pr-3' | AGACUUAGCUCCCUGAAAU | 27 | AUUUCAGGGAGCUAAGUCU | 49 |
| SIRT1-Pr-4' | CGUGUAGUGCAGCCAAAUU | 28 | AAUUUGGCUGCACUACACG | 50 |
| SIRT1-Pr-5' | UCGUCUUCGUCGUACAAGU | 29 | ACUUGUACGACGAAGACGA | 51 |
| SIRT1-Tr-NM_012238-Pr-57-Cp-0' | AUAUGCCUCCUGGGAAGA | 30 | UCUUCCCAGGAGGACAUAU | 52 |
| SIRT1-Tr-NM_012238-Pr-232-Cp-0' | GCCGGAACAGGUCAAGUUU | 31 | AAACUUGAGCUGUUCCGGC | 53 |
| SIRT1-Tr-NM_012238-Pr-89-Cp-0' | UUUCUAUCUGUUUAAAGGA | 32 | UCCUUUAAACAGAUAGAAA | 54 |
| SIRT1-Tr-NM_012238-Pr-87-Cp-0' | CCAUAUAACCCAUGGUAGA | 33 | UCUACCAUGGGUUAUAUGG | 55 |
| SIRT1.NM_012238-Pr-6' | GCUUCAACGUGUGUGAAU | 34 | AUUCACACACGUUUGAAGC | 56 |
| SIRT1.NM_012238-Pr-17' | AGCCGUUUCUAAACUUAAU | 35 | AUUAAGUUUAGAAACGGCU | 57 |
| SIRT1.NM_012238-Pr-19' | CUGAAAUACGUUGGAUAGU | 36 | ACUAUCCAACGUAUUUCAG | 58 |
| SIRT1.NM_012238-Pr-30' | GUUGGAUAGUCGUUCUGUU | 37 | AACAGAACGACUAUCCAAC | 59 |

TABLE 3-continued

Sequences of SIRT1-saRNAs (with no 3' overhang)

| saRNA ID | Sense sequence | SEQ ID No. | Antisense sequence | SEQ ID No. |
| --- | --- | --- | --- | --- |
| SIRT1.NM_012238-Pr-38' | UGCCUUAGCCUUGUCUAUA | 38 | UAUAGACAAGGCUAAGGCA | 60 |
| SIRT1.NM_012238-Pr-39' | CUAGCCGUUUCUAAACUUA | 39 | UAAGUUUAGAAACGGCUAG | 61 |
| SIRT1.NM_001142498-Pr-1' | GACUUAGCUCCCUGAAAUA | 25 | UAUUUCAGGGAGCUAAGUC | 47 |
| SIRT1.NM_001142498-Pr-2' | AGACUUAGCUCCCUGAAAU | 27 | AUUUCAGGGAGCUAAGUCU | 49 |
| SIRT1.NM_001142498-Pr-13' | GCAAGCUGUGACUAUAGA | 40 | UUCUAUAGUCACAGCUUGC | 62 |
| SIRT1.NM_001142498-Pr-18' | GUGUUAAGUUUGUGUCUCA | 41 | UGAGACACAAACUUAACAC | 63 |
| SIRT1.NM_001142498-Pr-19' | GCCUUAGCCUUGUCUAUAU | 26 | AUAUAGACAAGGCUAAGGC | 48 |
| SIRT1.NM_001142498-Pr-23' | UGCUAGAAGUGUUAAGUUU | 42 | AAACUUAACACUUCUAGCA | 64 |
| SIRT1.NM_001142498-Pr-24' | CAGCCACGUUCUUUAAAUU | 43 | AAUUUAAAGAACGUGGCUG | 65 |
| SIRT1.NM_001142498-Pr-25' | CUGAAAUACGUUGGAUAGU | 36 | ACUAUCCAACGUAUUUCAG | 58 |
| SIRT1.NM_001142498-Pr-26' | AAGUUUGUGUCUCAAUACU | 44 | AGUAUUGAGACACAAACUU | 66 |
| SIRT1.NM_001142498-Pr-34' | GUUGGAUAGUCGUUCUGUU | 37 | AACAGAACGACUAUCCAAC | 59 |
| SIRT1.NM_001142498-Pr-36' | AGAGCAAGAUUAGAAUAAA | 45 | UUUAUUCUAAUCUUGCUCU | 67 |
| SIRT1.NM_001142498-Pr-37' | UGCAUUACAGAAUGGUAAU | 46 | AUUACCAUUCUGUAAUGCA | 68 |

TABLE 4

Sequences of SIRT1-saRNAs (with 3' overhang)

| saRNA ID | Sense sequence (with UU) | SEQ ID No. | Antisense sequence (with UU) | SEQ ID No. |
|---|---|---|---|---|
| SIRT1-Pr-1 | GACUUAGCUCCCUGAAAUAUU | 69 | UAUUUCAGGGAGCUAAGUCUU | 91 |
| SIRT1-Pr-2 | GCCUUAGCCUUGUCUAUAUUU | 70 | AUAUAGACAAGGCUAAGGCUU | 92 |
| SIRT1-Pr-3 | AGACUUAGCUCCCUGAAAUUU | 71 | AUUUCAGGGAGCUAAGUCUUU | 93 |
| SIRT1-Pr-4 | CGUGUAGUGCAGCCAAAUUUU | 72 | AAUUUGGCUGCACUACACGUU | 94 |
| SIRT1-Pr-5 | UCGUCUUCGUCGUACAAGUUU | 73 | ACUUGUACGACGAAGACGAUU | 95 |
| SIRT1-Tr-NM_012238-Pr-57-Cp-0 | AUAUGUCCUCCUGGGAAGA[mU][mU] | 74 | UCUUCCCAGGAGGACAUAU[mU][mU] | 96 |
| SIRT1-Tr-NM_012238-Pr-232-Cp-0 | GCCGGAACAGCUCAAGUUU[mU][mU] | 75 | AAACUUGAGCUGUUCCGGC[mU][mU] | 97 |
| SIRT1-Tr-NM_012238-Pr-89-Cp-0 | UUUCUAUCUGUUUAAAGGA[mU][mU] | 76 | UCCUUUAAACAGAUAGAAA[mU][mU] | 98 |
| SIRT1-Tr-NM_012238-Pr-87-Cp-0 | CCAUAUAACCCAUGGUAGA[mU][mU] | 77 | UCUACCAUGGGUUAUAUGG[mU][mU] | 99 |
| SIRT1.NM_012238-Pr-6 | GCUUCAAACGUGUGUGAAUUU | 78 | AUUCACACACGUUUGAAGCUU | 100 |
| SIRT1.NM_012238-Pr-17 | AGCCGUUUCUAAACUUAAUUU | 79 | AUUAAGUUUAGAAACGGCUUU | 101 |
| SIRT1.NM_012238-Pr-19 | CUGAAAUACGUUGGAUAGUUU | 80 | ACUAUCCAACGUAUUUCAGUU | 102 |
| SIRT1.NM_012238-Pr-30 | GUUGGAUAGUCGUUCUGUUUU | 81 | AACAGAACGACUAUCCAACUU | 103 |
| SIRT1.NM_012238-Pr-38 | UGCCUUAGCCUUGUCUAUAUU | 82 | UAUAGACAAGGCUAAGGCAUU | 104 |
| SIRT1.NM_012238-Pr-39 | CUAGCCGUUUCUAAACUUAUU | 83 | UAAGUUUAGAAACGGCUAGUU | 105 |
| SIRT1.NM_001142498-Pr-1 | GACUUAGCUCCCUGAAAUAUU | 69 | UAUUUCAGGGAGCUAAGUCUU | 91 |
| SIRT1.NM_001142498-Pr-2 | AGACUUAGCUCCCUGAAAUUU | 71 | AUUUCAGGGAGCUAAGUCUUU | 93 |
| SIRT1.NM_001142498-Pr-13 | GCAAGCUGUGACUAUAGAAUU | 84 | UUCUAUAGUCACAGCUUGCUU | 106 |
| SIRT1.NM_001142498-Pr-18 | GUGUUAAGUUUGUGUCUCAUU | 85 | UGAGACACAAACUUAACACUU | 107 |
| SIRT1.NM_001142498-Pr-19 | GCCUUAGCCUUGUCUAUAUUU | 70 | AUAUAGACAAGGCUAACGCUU | 92 |
| SIRT1.NM_001142498-Pr-23 | UGCUAGAAGUGUUAAGUUUUU | 86 | AAACUUAACACUUCUAGCAUU | 108 |
| SIRT1.NM_001142498-Pr-24 | CAGCCACGUUCUUUAAAUUUU | 87 | AAUUUAAAGAACGUGGCUGUU | 109 |
| SIRT1.NM_001142498-Pr-25 | CUGAAAUACGUUGGAUAGUUU | 80 | ACUAUCCAACGUAUUUCAGUU | 102 |
| SIRT1.NM_001142498-Pr-26 | AAGUUUGUGUCUCAAUACUUU | 88 | AGUAUUGAGACACAAACUUUU | 110 |

TABLE 4-continued

Sequences of SIRT1-saRNAs (with 3' overhang)

| saRNA ID | Sense sequence (with UU) | SEQ ID No. | Antisense sequence (with UU) | SEQ ID No. |
|---|---|---|---|---|
| SIRT1.NM_001142498-Pr-34 | GUUGGAUAGUCGUUCUGUUUU | 81 | AACAGAACGACUAUCCAACUU | 103 |
| SIRT1.NM_001142498-Pr-36 | AGAGCAAGAUUAGAAUAAAUU | 89 | UUUAUUCUAAUCUUGCUCUUU | 111 |
| SIRT1.NM_001142498-Pr-37 | UGCAUUACAGAAUGGUAAUUU | 90 | AUUACCAUUCUGUAAUGCAUU | 112 |

*[mU]: 2'-OMethyl (2'-OMe) modified uridine.

The method disclosed in US 2013/0164846 filed Jun. 23, 2011 (saRNA algorithm), the contents of which are incorporated herein by reference in their entirety, may also be used to design saRNA. The design of saRNA is also disclosed in U.S. Pat. Nos. 8,324,181 and 7,709,566 to Corey et al., US Pat. Pub. No. 2010/0210707 to Li et al., and Voutila et al., *Mol Ther Nucleic Acids*, vol. 1, e35 (2012), the contents of each of which are incorporated herein by reference in their entirety.

The saRNA of the present invention may be produced by any suitable method, for example synthetically or by expression in cells using standard molecular biology techniques which are well-known to a person of ordinary skill in the art. For example, the saRNA of the present invention may be chemically synthesized or recombinantly produced using methods known in the art.

Bifunction Oligonucleotides

Bifunction or dual-functional oligonucleotides, e.g., saRNA may be designed to up-regulate the expression of a first gene and down-regulate the expression of at least one second gene. One strand of the dual-functional oligonucleotide activates the expression of the first gene and the other strand inhibits the expression of the second gene. Each strand might further comprise a Dicer substrate sequence.

Chemical Modifications of saRNA

Herein, in saRNA, the terms "modification" or, as appropriate, "modified" refer to structural and/or chemical modifications with respect to A, G, U or C ribonucleotides. Nucleotides in the saRNAs of the present invention may comprise non-standard nucleotides, such as non-naturally occurring nucleotides or chemically synthesized nucleotides or deoxynucleotides. The saRNA of the present invention may include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof. In a non-limiting example, the 2'-OH of U is substituted with 2'-OMe.

In one embodiment, the saRNAs of the present invention may comprise at least one modification described herein.

In another embodiment, the saRNA is an saRNA duplex and the sense strand and antisense sequence may independently comprise at least one modification. As a non-limiting example, the sense sequence may comprise a modification and the antisense strand may be unmodified. As another non-limiting example, the antisense sequence may comprise a modification and the sense strand may be unmodified. As yet another non-limiting example, the sense sequence may comprise more than one modification and the antisense strand may comprise one modification. As a non-limiting example, the antisense sequence may comprise more than one modification and the sense strand may comprise one modification.

The saRNA of the present invention can include a combination of modifications to the sugar, the nucleobase, and/or the internucleoside linkage. These combinations can include any one or more modifications described herein or in International Application Publication WO2013/052523 filed Oct. 3, 2012, in particular Formulas (Ia)-(Ia-5), (Ib)-(If), (IIa)-(IIp), (IIb-1), (IIb-2), (IIc-1)-(IIc-2), (IIn-1), (IIn-2), (IVa)-(IV1), and (IXa)-(IXr)), the contents of which are incorporated herein by reference in their entirety.

The saRNA of the present invention may or may not be uniformly modified along the entire length of the molecule. For example, one or more or all types of nucleotide (e.g., purine or pyrimidine, or any one or more or all of A, G, U, C) may or may not be uniformly modified in the saRNA of the invention. In some embodiments, all nucleotides X in an saRNA of the invention are modified, wherein X may be any one of nucleotides A, G, U, C, or any one of the combinations A+G, A+U, A+C, G+U, G+C, U+C, A+G+U, A+G+C, G+U+C or A+G+C.

Different sugar modifications, nucleotide modifications, and/or internucleoside linkages (e.g., backbone structures) may exist at various positions in an saRNA. One of ordinary skill in the art will appreciate that the nucleotide analogs or other modification(s) may be located at any position(s) of an saRNA such that the function of saRNA is not substantially decreased. The saRNA of the present invention may contain from about 1% to about 100% modified nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the saRNA of the present invention may be modified to be a circular nucleic acid. The terminals of the saRNA of the present invention may be linked by chemical reagents or enzymes, producing circular saRNA that has no free ends. Circular saRNA is expected to be more stable than its linear counterpart and to be resistant to digestion with RNase R exonuclease. Circular saRNA may further comprise other structural and/or chemical modifications with respect to A, G, U or C ribonucleotides.

The saRNA of the present invention may be modified with any modifications of an oligonucleotide or polynucleotide disclosed in pages 136 to 247 of PCT Publication WO2013/151666 published Oct. 10, 2013, the contents of which are incorporated herein by reference in their entirety.

The saRNA of the present invention may comprise a combination of modifications. The saRNA may comprise at least 2, 3, 4, 5, 6, 7, 8, 9, 10, 11, 12, 13, 14, 15, 16, 17, 18, 19, 20, 21, 22, 23, 24, 25, 26, 27, 28, 29 or 30 modifications for each strand.

In some embodiments, the saRNA is at least 50% modified, e.g., at least 50% of the nucleotides are modified. In some embodiments, the saRNA is at least 75% modified, e.g., at least 75% of the nucleotides are modified. In some embodiments, both strands of the saRNA may be modified across the whole length (100% modified). It is to be understood that since a nucleotide (sugar, base and phosphate moiety, e.g., linker) may each be modified, any modification to any portion of a nucleotide, or nucleoside, will constitute a modification.

In some embodiments, the saRNA is at least 10% modified in only one component of the nucleotide, with such component being selected from the nucleobase, sugar or linkage between nucleosides. For example, modifications of an saRNA may be made to at least 10%, 20%, 30%, 40%, 50%, 60%, 70%, 80%, 90% or 100% of the nucleobases, sugars or linkages of said saRNA.

In some embodiments, the saRNA comprises at least one sugar modification. Nonlimiting examples of the sugar modification may include the following:

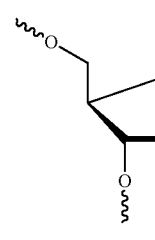
DNA

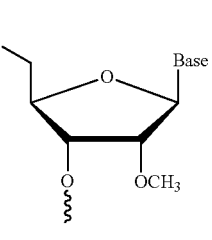
2'-O—Me

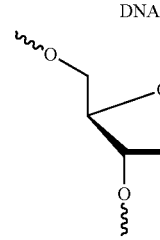
2'F-RNA

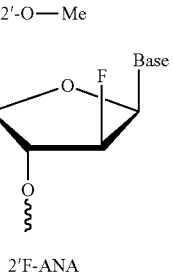
2'F-ANA

-continued

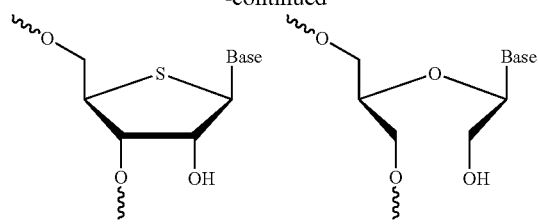
2'S-RNA    UNA

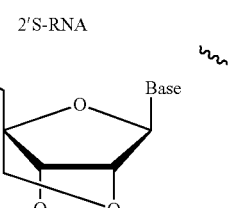
UNA

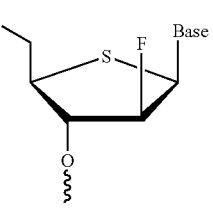
4'S-FANA

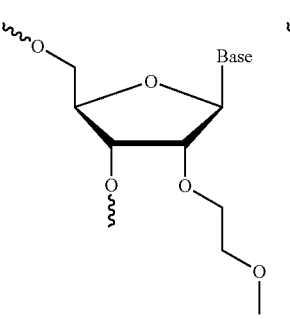
2'-O—MOE

2'-O-Allyl

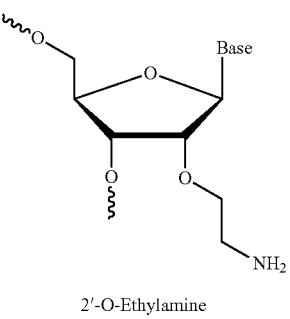
2'-O-Ethylamine

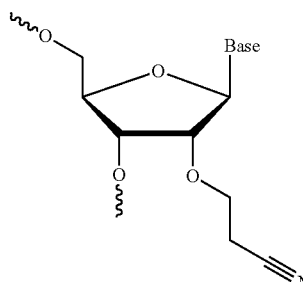
2'-O-Cyanoethyl

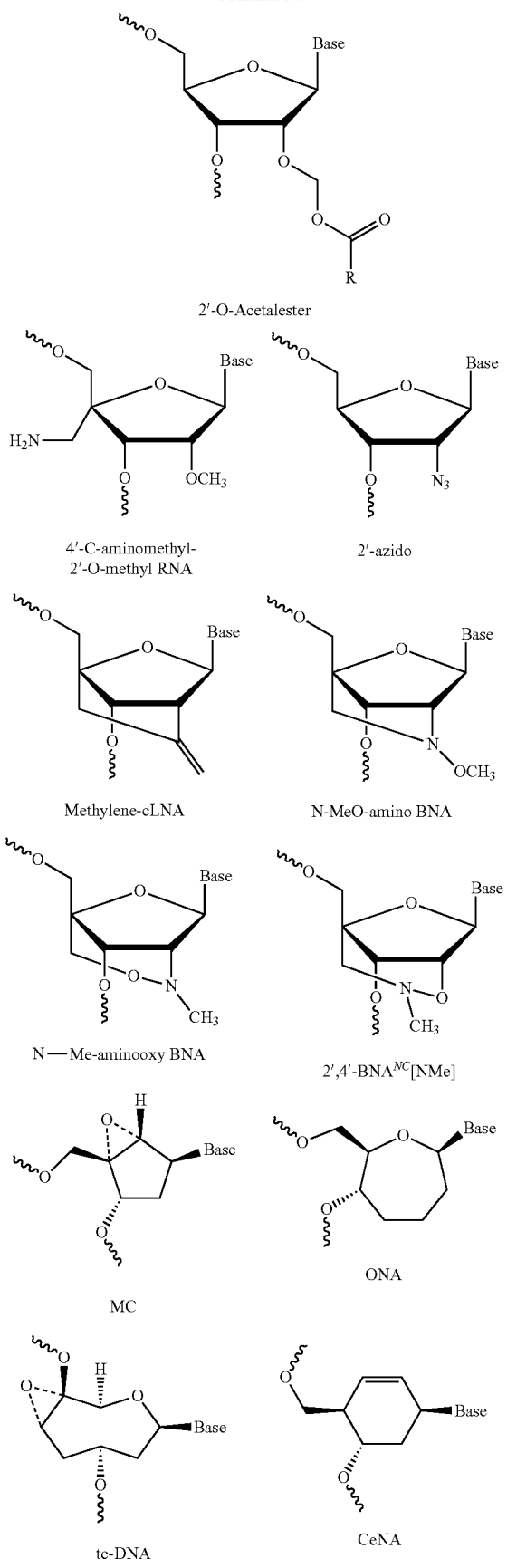

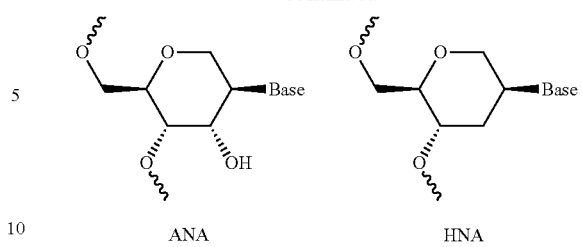

In some embodiments, at least one of the 2' positions of the sugar (OH in RNA or H in DNA) of a nucleotide of the saRNA is substituted with —OMe, referred to as 2'-OMe.

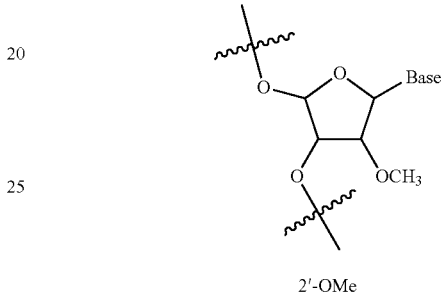

In some embodiments, at least one of the 2' positions of the sugar (OH in RNA or H in DNA) of a nucleotide of the saRNA is substituted with —F, referred to as 2'-F.

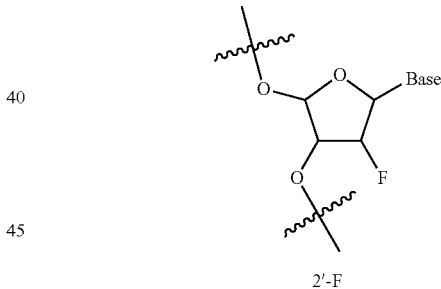

In some embodiments, the saRNA comprises at least one phosphorothioate linkage or methylphosphonate linkage between nucleotides.

In some embodiments, the saRNA comprises 3' and/or 5' capping or overhang. In some embodiments, the saRNA of the present invention may comprise at least one inverted deoxyribonucleoside overhang (e.g., dT). The inverted overhang, e.g., dT, may be at the 5' terminus or 3' terminus of the passenger (sense) strand. In some embodiments, the saRNA of the present invention may comprise inverted abasic modifications on the passenger strand. The at least one inverted abasic modification may be on 5' end, or 3' end, or both ends of the passenger strand. The inverted abasic modification may encourage preferential loading of the guide (antisense) strand.

In some embodiments, the saRNA comprises at least one 5'-(E)-vinylphosphonate (5'-E-VP) modification.

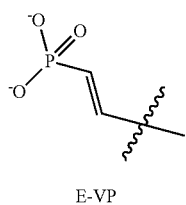

E-VP

In some embodiments, the saRNA comprises at least one glycol nucleic acid (GNA), an acyclic nucleic acid analogue, as a modification.

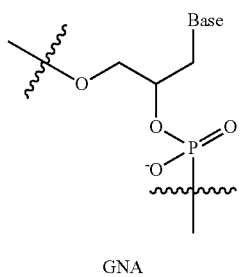

GNA saRNA Conjugates and Combinations

Conjugation may result in increased stability and/or half-life and may be particularly useful in targeting the saRNA of the present invention to specific sites in the cell, tissue or organism. The saRNA of the present invention can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug. Suitable conjugates for nucleic acid molecules are disclosed in International Publication WO 2013/090648 filed Dec. 14, 2012, the contents of which are incorporated herein by reference in their entirety.

According to the present invention, saRNA of the present invention may be administered with, or further include one or more of RNAi agents, small interfering RNAs (siRNAs), small hairpin RNAs (shRNAs), long non-coding RNAs (lncRNAs), enhancer RNAs, enhancer-derived RNAs or enhancer-driven RNAs (eRNAs), microRNAs (miRNAs), miRNA binding sites, antisense RNAs, ribozymes, catalytic DNA, tRNA, RNAs that induce triple helix formation, aptamers or vectors, and the like to achieve different functions. The one or more RNAi agents, small interfering RNAs (siRNAs), small hairpin RNAs (shRNAs), long non-coding RNAs (lncRNA), microRNAs (miRNAs), miRNA binding sites, antisense RNAs, ribozymes, catalytic DNA, tRNA, RNAs that induce triple helix formation, aptamers or vectors may comprise at least one modification or substitution.

In some embodiments, the modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; conjugation to a high molecular weight, non-immunogenic compound; conjugation to a lipophilic compound; and incorporation of phosphorothioate into the phosphate backbone. In one embodiment, the high molecular weight, non-immunogenic compound is polyalkylene glycol, or polyethylene glycol (PEG).

In one embodiment, saRNA of the present invention may be attached to a transgene so it can be co-expressed from an RNA polymerase II promoter. In a non-limiting example, saRNA of the present invention is attached to green fluorescent protein gene (GFP).

In one embodiment, saRNA of the present invention may be attached to a DNA or RNA aptamer, thereby producing saRNA-aptamer conjugate. Aptamers are oligonucleotides or peptides with high selectivity, affinity and stability. They assume specific and stable three-dimensional shapes, thereby providing highly specific, tight binding to target molecules. An aptamer may be a nucleic acid species that has been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Nucleic acid aptamers have specific binding affinity to molecules through interactions other than classic Watson-Crick base pairing. Nucleic acid aptamers, like peptides generated by phage display or monoclonal antibodies (mAbs), are capable of specifically binding to selected targets and, through binding, block their targets' ability to function. In some cases, aptamers may also be peptide aptamers. For any specific molecular target, nucleic acid aptamers can be identified from combinatorial libraries of nucleic acids, e.g. by SELEX. Peptide aptamers may be identified using a yeast two hybrid system. A skilled person is therefore able to design suitable aptamers for delivering the saRNAs or cells of the present invention to target cells such as liver cells. DNA aptamers, RNA aptamers and peptide aptamers are contemplated. Administration of saRNA of the present invention to the liver using liver-specific aptamers is preferred.

As used herein, a typical nucleic acid aptamer is approximately 10-15 kDa in size (20-45 nucleotides), binds its target with at least nanomolar affinity, and discriminates against closely related targets. Nucleic acid aptamers may be ribonucleic acid, deoxyribonucleic acid, or mixed ribonucleic acid and deoxyribonucleic acid. Aptamers may be single-stranded ribonucleic acid, deoxyribonucleic acid or mixed ribonucleic acid and deoxyribonucleic acid. Aptamers may comprise at least one chemical modification.

A suitable nucleotide length for an aptamer ranges from about 15 to about 100 nucleotides (nt), and in various other embodiments, 15-30 nt, 20-25 nt, 30-100 nt, 30-60 nt, 25-70 nt, 25-60 nt, 40-60 nt, 25-40 nt, 30-40 nt, any of 22, 23, 24, 25, 26, 27, 28, 29, 30, 31, 32, 33, 34, 35, 36, 37, 38, 39 or 40 nt or 40-70 nt in length. However, the sequence can be designed with sufficient flexibility such that it can accommodate interactions of aptamers with two targets at the distances described herein. Aptamers may be further modified to provide protection from nuclease and other enzymatic activities. The aptamer sequence can be modified by any suitable methods known in the art.

The saRNA-aptamer conjugate may be formed using any known method for linking two moieties, such as direct chemical bond formation, linkage via a linker such as streptavidin and so on.

In one embodiment, saRNA of the present invention may be attached to an antibody. Methods of generating antibodies against a target cell surface receptor are well known. The saRNAs of the invention may be attached to such antibodies with known methods, for example using RNA carrier proteins. The resulting complex may then be administered to a subject and taken up by the target cells via receptor-mediated endocytosis.

In one embodiment, saRNA of the present invention may be conjugated with lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-5-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937), the content of each of which is herein incorporated by reference in its entirety.

In one embodiment, the saRNA of the present invention is conjugated with a ligand. In one non-limiting example, the ligand may be any ligand disclosed in US 20130184328 to Manoharan et al., the contents of which are incorporated herein by reference in their entirety. The conjugate has a formula of Ligand-[linker]$_{optional}$-[tether]$_{optional}$-oligonucleotide agent. The oligonucleotide agent may comprise a subunit having formulae (I) disclosed by US 20130184328 to Manoharan et al., the contents of which are incorporated herein by reference in their entirety. In another non-limiting example, the ligand may be any ligand disclosed in US 20130317081 to Akinc et al., the contents of which are incorporated herein by reference in their entirety, such as a lipid, a protein, a hormone, or a carbohydrate ligand of Formula II-XXVI. The ligand may be coupled with the saRNA with a bivalent or trivalent branched linker in Formula XXXI-XXXV disclosed in Akinc.

Representative U.S. patents that teach the preparation of such nucleic acid/lipid conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, the content of each of which is herein incorporated by reference in its entirety.

The saRNA of the present invention may be provided in combination with other active ingredients known to have an effect in the particular method being considered. The other active ingredients may be administered simultaneously, separately, or sequentially with the saRNA of the present invention. In one embodiment, saRNA of the present invention is administered with saRNA modulating a different target gene.

In on embodiment, the saRNA is conjugated with a carbohydrate ligand, such as any carbohydrate ligand disclosed in U.S. Pat. Nos. 8,106,022 and 8,828,956 to Manoharan et al. (Alnylam Pharmaceuticals), the contents of which are incorporated herein by reference in their entirety. For example, the carbohydrate ligand may be monosaccharide, disaccharide, trisaccharide, tetrasaccharide, oligosaccharide, or polysaccharide. These carbohydrate-conjugated RNA agents may target the parenchymal cells of the liver. In one embodiment, the saRNA is conjugated with more than one carbohydrate ligand, preferably two or three. In one embodiment, the saRNA is conjugated with one or more galactose moiety. In another embodiment, the saRNA is conjugated at least one (e.g., two or three or more) lactose molecules (lactose is a glucose coupled to a galactose). In another embodiment, the saRNA is conjugated with at least one (e.g., two or three or more) N-Acetyl-Galactosamine (GalNAc), N-Ac-Glucosamine (GluNAc), or mannose (e.g., mannose-6-phosphate). In one embodiment, the saRNA is conjugated with at least one mannose ligand, and the conjugated saRNA targets macrophages.

In one embodiment, saRNA of the present invention is administered with a small interfering RNA or siRNA that inhibits the expression of a gene.

In one embodiment, saRNA of the present invention is administered with one or more drugs for therapeutic purposes.

II. Composition of the Invention

One aspect of the present invention provides pharmaceutical compositions comprising a small activating RNA (saRNA) that upregulates a target gene, and at least one pharmaceutically acceptable carrier.

Formulation, Delivery, Administration, and Dosing

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, compositions are administered to humans, human patients or subjects. For the purposes of the present disclosure, the phrase "active ingredient" generally refers to saRNA to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the formulations described herein may contain at least one saRNA. As a non-limiting example, the formulations may contain 1, 2, 3, 4 or 5 saRNAs with different sequences. In one embodiment, the formulation contains at least three saRNAs with different sequences. In one embodiment, the formulation contains at least five saRNAs with different sequences.

The saRNA of the present invention can be formulated using one or more excipients to: (1) increase stability; (2) increase cell transfection; (3) permit the sustained or delayed release (e.g., from a depot formulation of the saRNA); (4) alter the biodistribution (e.g., target the saRNA to specific tissues or cell types); (5) increase the translation of encoded protein in vivo; and/or (6) alter the release profile of encoded protein in vivo.

In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with saRNA (e.g., for transplantation into a subject), hyaluronidase, nanoparticle mimics and combinations thereof. Accordingly, the formulations of the invention can include one or more excipients, each in an amount that together increases the stability of the saRNA and/or increases cell transfection by the saRNA. Further, the saRNA of the present invention may be formulated using self-assembled nucleic acid nanoparticles. Pharmaceutically acceptable carriers, excipients, and delivery agents for nucleic acids that may be used in the formulation with the saRNA of the present invention are disclosed in International Publication WO 2013/090648 filed Dec. 14, 2012, the contents of which are incorporated herein by reference in their entirety.

In one embodiment, the saRNA of the present invention comprises two single RNA strands that are 21 nucleotides in length each that are annealed to form a double-stranded saRNA as the active ingredient. The composition further comprises a salt buffer composed of 50 mM Tris-HCl, pH 8.0, 100 mM NaCl and 5 mM EDTA.

In another embodiment, the saRNA of the present invention may be delivered with dendrimers. Dendrimers are highly branched macromolecules. In one embodiment, the saRNA of the present invention is complexed with structurally flexible poly(amidoamine) (PAMAM) dendrimers for targeted in vivo delivery. The complex is called saRNA-dendrimers. Dendrimers have a high degree of molecular uniformity, narrow molecular weight distribution, specific size and shape characteristics, and a highly-functionalized terminal surface. The manufacturing process is a series of repetitive steps starting with a central initiator core. Each subsequent growth step represents a new generation of polymers with a larger molecular diameter and molecular weight, and more reactive surface sites than the preceding generation.

PAMAM dendrimers are efficient nucleotide delivery systems that bear primary amine groups on their surface and also a tertiary amine group inside of the structure. The primary amine group participates in nucleotide binding and promotes their cellular uptake, while the buried tertiary amino groups act as a proton sponge in endosomes and enhance the release of nucleic acid into the cytoplasm. These dendrimers protect the saRNA carried by them from ribonuclease degradation and achieves substantial release of saRNA over an extended period of time via endocytosis for efficient gene targeting. The in vivo efficacy of these nanoparticles have previously been evaluated where biodistribution studies show that the dendrimers preferentially accumulate in peripheral blood mononuclear cells and live with no discernible toxicity (see Zhou et al., Molecular Ther. 2011 Vol. 19, 2228-2238, the contents of which are incorporated herein by reference in their entirety). PAMAM dendrimers may comprise a triethanolamine (TEA) core, a diaminobutane (DAB) core, a cystamine core, a diaminohexane (HEX) core, a diamonododecane (DODE) core, or an ethylenediamine (EDA) core. In one embodiment, PAMAM dendrimers comprise a TEA core or a DAB core.

Lipidoids

The synthesis of lipidoids has been extensively described and formulations containing these compounds are particularly suited for delivery of oligonucleotides or nucleic acids (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

While these lipidoids have been used to effectively deliver double-stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010; all of which is incorporated herein in their entirety), the present disclosure contemplates their formulation and use in delivering saRNA. Complexes, micelles, liposomes or particles can be prepared containing these lipidoids and therefore, can result in an effective delivery of the saRNA following the injection of a lipidoid formulation via localized and/or systemic routes of administration. Lipidoid complexes of saRNA can be administered by various means including, but not limited to, intravenous, intramuscular, or subcutaneous routes.

In vivo delivery of nucleic acids may be affected by many parameters, including, but not limited to, the formulation composition, nature of particle PEGylation, degree of loading, oligonucleotide to lipid ratio, and biophysical parameters such as, but not limited to, particle size (Akinc et al., Mol Ther. 2009 17:872-879; the contents of which are herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010); the contents of which are herein incorporated by reference in its entirety), C12-200 (including derivatives and variants), and MD1, can be tested for in vivo activity.

The lipidoid referred to herein as "98N12-5" is disclosed by Akinc et al., Mol Ther. 2009 17:872-879 and the contents of which is incorporated by reference in its entirety.

The lipidoid referred to herein as "C12-200" is disclosed by Love et al., Proc Natl Acad Sci USA. 2010 107:1864-1869 and Liu and Huang, Molecular Therapy. 2010 669-670; the contents of both of which are herein incorporated by reference in their entirety. The lipidoid formulations can include particles comprising either 3 or 4 or more components in addition to the saRNA. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

In one embodiment, a saRNA formulated with a lipidoid for systemic intravenous administration can target the liver. For example, a final optimized intravenous formulation using saRNA and comprising a lipid molar composition of 42% 98N12-5, 48% cholesterol, and 10% PEG-lipid with a final weight ratio of about 7.5 to 1 total lipid to saRNA and a C14 alkyl chain length on the PEG lipid, with a mean particle size of roughly 50-60 nm, can result in the distribution of the formulation to be greater than 90% to the liver. (see, Akinc et al., Mol Ther. 2009 17:872-879; the contents of which are herein incorporated by reference in its entirety). In another example, an intravenous formulation using a C12-200 (see published international application WO2010129709, the contents of which is herein incorporated by reference in their entirety) lipidoid may have a molar ratio of 50/10/38.5/1.5 of C12-200/disteroylphosphatidyl choline/cholesterol/PEG-DMG, with a weight ratio of 7 to 1 total lipid to nucleic acid and a mean particle size of 80 nm may be effective to deliver saRNA (see, Love et al., Proc Natl Acad Sci USA. 2010 107:1864-1869, the contents of which are herein incorporated by reference in its entirety).

In another embodiment, an MD1 lipidoid-containing formulation may be used to effectively deliver saRNA to hepatocytes in vivo. The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879, the contents of which are herein incorporated by reference in its entirety), use of a lipidoid-formulated saRNA to deliver the formulation to other cells types including, but not limited to, endothelial cells, myeloid cells, and muscle cells may not be similarly size-limited.

Use of lipidoid formulations to deliver siRNA in vivo to other non-hepatocyte cells such as myeloid cells and endothelium has been reported (see Akinc et al., Nat Biotechnol. 2008 26:561-569; Leuschner et al., Nat Biotechnol. 2011 29:1005-1010; Cho et al. Adv. Funct. Mater. 2009 19:3112-3118; $8^{th}$ International Judah Folkman Conference, Cambridge, Mass. Oct. 8-9, 2010; the contents of each of which is herein incorporated by reference in its entirety). Effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of saRNA for delivery to different cell types including, but not limited to, hepatocytes, myeloid cells, muscle cells, etc. For example, the component molar ratio may include, but is not limited to, 50% C12-200, 10% disteroylphosphatidyl choline, 38.5% cholesterol, and %1.5 PEG-DMG (see Leuschner et al., Nat Biotechnol 2011 29:1005-1010; the contents of which are herein incorporated by reference in its entirety). The use of lipidoid formulations for the localized delivery of nucleic acids to cells (such as, but not limited to, adipose cells and muscle cells) via either subcutaneous or intramuscular delivery, may not require all of the formulation components desired for systemic delivery, and as such may comprise only the lipidoid and saRNA.

Liposomes, Lipoplexes, and Lipid Nanoparticles

The saRNA of the invention can be formulated using one or more liposomes, lipoplexes, or lipid nanoparticles. In one embodiment, pharmaceutical compositions of saRNA include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment, pharmaceutical compositions described herein may include, without limitation, liposomes such as those formed from 1,2-dioleyloxy-N,N-dimethyl-aminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; the contents of which are herein incorporated by reference in its entirety) and liposomes which may deliver small molecule drugs such as, but not limited to, DOXIL® from Janssen Biotech, Inc. (Horsham, Pa.).

In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles *Hum Gene Ther.* 2008 19:125-132; the contents of each of which are incorporated herein in their entireties). The original manufacture method by Wheeler et al. was a detergent dialysis method, which was later improved by Jeffs et al. and is referred to as the spontaneous vesicle formation method. The liposome formulations may be composed of 3 to 4 lipid components in addition to the saRNA. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. In another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethyl-aminopropane (DLenDMA), as described by Heyes et al. In another example, the nucleic acid-lipid particle may comprise a cationic lipid comprising from about 50 mol % to about 85 mol % of the total lipid present in the particle; a non-cationic lipid comprising from about 13 mol % to about 49.5 mol % of the total lipid present in the particle; and a conjugated lipid that inhibits aggregation of particles comprising from about 0.5 mol % to about 2 mol % of the total lipid present in the particle as described in WO2009127060 to Maclachlan et al, the contents of which are incorporated herein by reference in their entirety. In another example, the nucleic acid-lipid particle may be any nucleic acid-lipid particle disclosed in US2006008910 to Maclachlan et al., the contents of which are incorporated herein by reference in their entirety. As a non-limiting example, the nucleic acid-lipid particle may comprise a cationic lipid of Formula I, a non-cationic lipid, and a conjugated lipid that inhibits aggregation of particles.

In one embodiment, the saRNA of the present invention may be formulated in a lipid vesicle which may have crosslinks between functionalized lipid bilayers.

In one embodiment, the liposome may contain a sugar-modified lipid disclosed in U.S. Pat. No. 5,595,756 to Bally et al., the contents of which are incorporated herein by reference in their entirety. The lipid may be a ganglioside and cerebroside in an amount of about 10 mol percent.

In one embodiment, the saRNA of the present invention may be formulated in a liposome comprising a cationic lipid. The liposome may have a molar ratio of nitrogen atoms in the cationic lipid to the phosphates in the saRNA (N:P ratio) of between 1:1 and 20:1 as described in International Publication No. WO2013006825, the contents of which are herein incorporated by reference in its entirety. In another embodiment, the liposome may have a N:P ratio of greater than 20:1 or less than 1:1.

In one embodiment, the saRNA of the present invention may be formulated in a lipid-polycation complex. The formation of the lipid-polycation complex may be accomplished by methods known in the art and/or as described in U.S. Pub. No. 20120178702, the contents of which are herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326; herein incorporated by reference in its entirety. In another embodiment, the saRNA may be formulated in a lipid-polycation complex which may further include a neutral lipid such as, but not limited to, cholesterol or dioleoyl phosphatidylethanolamine (DOPE).

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; the contents of which are herein incorporated by reference in its entirety), the liposome formulation was composed of 57.1% cationic lipid, 7.1% dipalmitoylphosphatidylcholine, 34.3% cholesterol, and 1.4% PEG-c-DMA.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain 1-5% of the lipid molar ratio of PEG-c-DOMG as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol) or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the saRNA of the present invention may be formulated in a lipid nanoparticle such as the lipid nanoparticles described in International Publication No.

WO2012170930, the contents of which are herein incorporated by reference in its entirety.

In one embodiment, the cationic lipid which may be used in formulations of the present invention may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865 and WO2008103276, U.S. Pat. Nos. 7,893,302, 7,404,969 and 8,283,333 and US Patent Publication No. US20100036115 and US20120202871; the contents of each of which is herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365 and WO2012044638; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXXII of U.S. Pat. No. 7,404,969 and formula I-VI of US Patent Publication No. US20100036115; the contents of each of which are herein incorporated by reference in their entirety. In yet another embodiment, the cationic lipid may be a multivalent cationic lipid such as the cationic lipid disclosed in U.S. Pat. No. 7,223,887 to Gaucheron et al., the contents of which are incorporated herein by reference in their entirety. The cationic lipid may have a positively-charged head group including two quaternary amine groups and a hydrophobic portion including four hydrocarbon chains as described in U.S. Pat. No. 7,223,887 to Gaucheron et al., the contents of which are incorporated herein by reference in their entirety. In yet another embodiment, the cationic lipid may be biodegradable as the biodegradable lipids disclosed in US20130195920 to Maier et al., the contents of which are incorporated herein by reference in their entirety. The cationic lipid may have one or more biodegradable groups located in a lipidic moiety of the cationic lipid as described in formula I-IV in US 20130195920 to Maier et al., the contents of which are incorporated herein by reference in their entirety.

As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (I9Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl] pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine,N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, I-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoylo ctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine and (11E,20Z,23Z)—N,N-dimethylnonacosa-l1,20,2-trien-10-amine or a pharmaceutically acceptable salt or stereoisomer thereof.

In one embodiment, the lipid may be a cleavable lipid such as those described in International Publication No. WO2012170889, the contents of which are herein incorporated by reference in their entirety.

In one embodiment, the nanoparticles described herein may comprise at least one cationic polymer described herein and/or known in the art.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724 and WO201021865; the contents of each of which is herein incorporated by reference in their entirety.

In one embodiment, the LNP formulations of the saRNA may contain PEG-c-DOMG at 3% lipid molar ratio. In another embodiment, the LNP formulations of the saRNA may contain PEG-c-DOMG at 1.5% lipid molar ratio.

In one embodiment, the pharmaceutical compositions of the saRNA may include at least one of the PEGylated lipids described in International Publication No. 2012099755, the contents of which is herein incorporated by reference in its entirety.

In one embodiment, the LNP formulation may contain PEG-DMG 2000 (1,2-dimyristoyl-sn-glycero-3-phophoethanolamine-N-[methoxy(polyethylene glycol)-2000). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA vaccines, PNAS 2012; PMID: 22908294; herein incorporated by reference in its entirety). As another non-limiting example, the saRNA described herein may be formulated in a nanoparticle to be delivered by a parenteral route as described in U.S. Pub. No. 20120207845; the contents of which is herein incorporated by reference in its entirety. The cationic lipid may also be the cationic lipids disclosed in US20130156845 to Manoharan et al. and US 20130129785 to Manoharan et al., WO 2012047656 to Wasan et al., WO 2010144740 to Chen et al., WO 2013086322 to Ansell et al., or WO 2012016184 to Manoharan et al., the contents of each of which are incorporated herein by reference in their entirety.

In one embodiment, the saRNA of the present invention may be formulated with a plurality of cationic lipids, such as a first and a second cationic lipid as described in US20130017223 to Hope et al., the contents of which are incorporated herein by reference in their entirety. The first cationic lipid can be selected on the basis of a first property and the second cationic lipid can be selected on the basis of a second property, where the properties may be determined as outlined in US20130017223, the contents of which are herein incorporated by reference in its entirety. In one embodiment, the first and second properties are complementary.

In another embodiment, the saRNA may be formulated with a lipid particle comprising one or more cationic lipids and one or more second lipids, and one or more nucleic acids, wherein the lipid particle comprises a solid core, as described in US Patent Publication No. US20120276209 to Cullis et al., the contents of which are incorporated herein by reference in their entirety.

In one embodiment, the saRNA of the present invention may be complexed with a cationic amphiphile in an oil-in-water (o/w) emulsion such as described in EP2298358 to Satishchandran et al., the contents of which are incorporated herein by reference in their entirety. The cationic amphiphile may be a cationic lipid, modified or unmodified spermine, bupivacaine, or benzalkonium chloride and the oil may be a vegetable or an animal oil. As a non-limiting example, at least 10% of the nucleic acid-cationic amphiphile complex is in the oil phase of the oil-in-water emulsion (see e.g., the complex described in European Publication No. EP2298358 to Satishchandran et al., the contents of which are herein incorporated by reference in its entirety).

In one embodiment, the saRNA of the present invention may be formulated with a composition comprising a mixture of cationic compounds and neutral lipids. As a non-limiting example, the cationic compounds may be formula (I) disclosed in WO 1999010390 to Ansell et al., the contents of which are disclosed herein by reference in their entirety, and the neutral lipid may be selected from the group consisting of diacylphosphatidylcholine, diacylphosphatidylethanolamine, ceramide and sphingomyelin. In another non-limiting example, the lipid formulation may comprise a cationic lipid of formula A, a neutral lipid, a sterol and a PEG or PEG-modified lipid disclosed in US 20120101148 to Akinc et al., the contents of which are incorporated herein by reference in their entirety.

In one embodiment, the LNP formulation may be formulated by the methods described in International Publication Nos. WO2011127255 or WO2008103276, each of which are herein incorporated by reference in their entirety. As a non-limiting example, the saRNA of the present invention may be encapsulated in any of the lipid nanoparticle (LNP) formulations described in WO2011127255 and/or WO2008103276; the contents of each of which are herein incorporated by reference in their entirety.

In one embodiment, the LNP formulations described herein may comprise a polycationic composition. As a non-limiting example, the polycationic composition may be selected from formula 1-60 of US Patent Publication No. US20050222064; the contents of which is herein incorporated by reference in its entirety. In another embodiment, the LNP formulations comprising a polycationic composition may be used for the delivery of the saRNA described herein in vivo and/or in vitro.

In one embodiment, the LNP formulations described herein may additionally comprise a permeability enhancer molecule. Non-limiting permeability enhancer molecules are described in US Patent Publication No. US20050222064; the contents of which is herein incorporated by reference in its entirety.

In one embodiment, the pharmaceutical compositions may be formulated in liposomes such as, but not limited to, DiLa2 liposomes (Marina Biotech, Bothell, Wash.), SMARTICLES®/NOV340 (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); the contents of which is herein incorporated by reference in its entirety) and hyaluronan-coated liposomes (Quiet Therapeutics, Israel).

In some embodiments, the pharmaceutical compositions may be formulated with any amphoteric liposome disclosed in WO 2008/043575 to Panzner and U.S. Pat. No. 8,580,297 to Essler et al. (Marina Biotech), the contents of which are incorporated herein by reference in their entirety. The amphoteric liposome may comprise a mixture of lipids including a cationic amphiphile, an anionic amphiphile and optional one or more neutral amphiphiles. The amphoteric liposome may comprise amphoteric compounds based on amphiphilic molecules, the head groups of which being substituted with one or more amphoteric groups. In some embodiments, the pharmaceutical compositions may be formulated with an amphoteric lipid comprising one or more amphoteric groups having an isoelectric point between 4 and 9, as disclosed in US 20140227345 to Essler et al. (Marina Biotech), the contents of which are incorporated herein by reference in their entirety.

In some embodiments, the pharmaceutical composition may be formulated with liposomes comprising a sterol derivative as disclosed in U.S. Pat. No. 7,312,206 to Panzner, et al. (Novosom), the contents of which are incorporated herein by reference in their entirety. In some embodiments, the pharmaceutical composition may be formulated with amphoteric liposomes comprising at least one amphipathic cationic lipid, at least one amphipathic anionic lipid, and at least one neutral lipid, or liposomes comprise at least one amphipathic lipid with both a positive and a negative charge, and at least one neutral lipid, wherein the liposomes are stable at pH 4.2 and pH 7.5, as disclosed in U.S. Pat. No. 7,780,983 to Panzner et al. (Novosom), the contents of which are incorporated herein by reference in their entirety. In some embodiments, the pharmaceutical composition may be formulated with liposomes comprising a serum-stable mixture of lipids taught in US 20110076322 to Panzner et al, the contents of which are incorporated herein by reference in their entirety, capable of encapsulating the saRNA of the present invention. The lipid mixture comprises phosphatidylcholine and phosphatidylethanolamine in a ratio in the range of about 0.5 to about 8. The lipid mixture may also include pH sensitive anionic and cationic amphiphiles, such that the mixture is amphoteric, being negatively charged or neutral at pH 7.4 and positively charged at pH 4. The drug/lipid ratio may be adjusted to target the liposomes to particular organs or other sites in the body. In some embodiments, liposomes loaded with the saRNA of the present invention as cargo, are prepared by the method disclosed in US 20120021042 to Panzner et al., the contents of which are incorporated herein by reference in their entirety. The method comprises steps of admixing an aqueous solution of a polyanionic active agent and an alcoholic solution of one or more amphiphiles and buffering said admixture to an acidic pH, wherein the one or more amphiphiles are susceptible of forming amphoteric liposomes at the acidic pH, thereby to form amphoteric liposomes in suspension encapsulating the active agent.

The nanoparticle formulations may be a carbohydrate nanoparticle comprising a carbohydrate carrier and a nucleic acid molecule (e.g., saRNA). As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which is herein incorporated by reference in its entirety).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the saRNA may be formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles *Hum Gene Ther.* 2008 19:125-132; the contents of each of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133; the contents of each of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364; the contents of which is herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Cuff Drug Discov Technol. 2011 8:197-206; Musacchio and Torchilin, *Front Biosci.* 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; the contents of each of which are incorporated herein by reference in its entirety).

In one embodiment, the saRNA is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; the contents of which are herein incorporated by reference in its entirety).

In one embodiment, the saRNA of the present invention can be formulated for controlled release and/or targeted delivery. As used herein, "controlled release" refers to a pharmaceutical composition or compound release profile that conforms to a particular pattern of release to effect a therapeutic outcome. In one embodiment, the saRNA may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulated" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In another embodiment, the saRNA may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc., Deerfield, Ill.), PEG-based sealants, and COSEAL® (Baxter International, Inc., Deerfield, Ill.).

In another embodiment, the lipid nanoparticle may be encapsulated into any polymer known in the art which may form a gel when injected into a subject. As another non-limiting example, the lipid nanoparticle may be encapsulated into a polymer matrix which may be biodegradable.

In one embodiment, the saRNA formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the controlled release and/or targeted delivery formulation may comprise at least one degradable polyester which may contain polycationic side chains. Degradable polyesters include, but are not limited to, poly (serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the saRNA of the present invention may be formulated with a targeting lipid with a targeting moiety such as the targeting moieties disclosed in US20130202652 to Manoharan et al., the contents of which are incorporated herein by reference in their entirety. As a non-limiting example, the targeting moiety of formula I of US 20130202652 to Manoharan et al. may selected in order to favor the lipid being localized with a desired organ, tissue, cell, cell type or subtype, or organelle. Non-limiting targeting moieties that are contemplated in the present invention include transferrin, anisamide, an RGD peptide, prostate specific membrane antigen (PSMA), fucose, an antibody, or an aptamer.

In one embodiment, the saRNA of the present invention may be encapsulated in a therapeutic nanoparticle. Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286 and US20120288541 and U.S. Pat. Nos. 8,206,747, 8,293,276, 8,318,208 and 8,318,211; the contents of each of which are herein incorporated by reference in their entirety. In another embodiment, therapeutic polymer nanoparticles may be identified by the methods described in US Pub No. US20120140790, the contents of which are herein incorporated by reference in its entirety.

In one embodiment, the therapeutic nanoparticle may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the saRNA of the present invention (see International Pub No. 2010075072 and US Pub No. US20100216804, US20110217377 and US20120201859, the contents of each of which are herein incorporated by reference in their entirety).

In one embodiment, the therapeutic nanoparticles may be formulated to be target specific. As a non-limiting example, the therapeutic nanoparticles may include a corticosteroid (see International Pub. No. WO2011084518; the contents of which are herein incorporated by reference in its entirety). In one embodiment, the therapeutic nanoparticles may be formulated to be cancer specific. As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, the contents of each of which are herein incorporated by reference in their entirety.

In one embodiment, the nanoparticles of the present invention may comprise a polymeric matrix. As a nonlimiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which is herein incorporated by reference in its entirety).

In one embodiment, the therapeutic nanoparticle may comprise a multiblock copolymer such as, but not limited to the multiblock copolymers described in U.S. Pat. Nos. 8,263,665 and 8,287,910; the contents of each of which are herein incorporated by reference in its entirety.

In one embodiment, the block copolymers described herein may be included in a polyion complex comprising a non-polymeric micelle and the block copolymer. (See e.g., U.S. Pub. No. 20120076836; the contents of which are herein incorporated by reference in its entirety).

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In one embodiment, the therapeutic nanoparticles may comprise at least one amine-containing polymer such as, but not limited to polylysine, polyethylene imine, poly(amidoamine) dendrimers, poly(beta-amino esters) (See e.g., U.S. Pat. No. 8,287,849; the contents of which are herein incorporated by reference in its entirety) and combinations thereof.

In one embodiment, the therapeutic nanoparticles may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, Cancer Res. 2006 66:6732-6740; the contents of which are herein incorporated by reference in its entirety).

In one embodiment, the therapeutic nanoparticle may be formulated in an aqueous solution which may be used to target cancer (see International Pub No. WO2011084513 and US Pub No. US20110294717, the contents of each of which is herein incorporated by reference in their entirety).

In one embodiment, the saRNA may be encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and US Pub. Nos. US20110262491, US20100104645, US20100087337 and US20120244222, the contents of each of which are herein incorporated by reference in their entirety. The synthetic nanocarriers may be formulated using methods known in the art and/or described herein. As a non-limiting example, the synthetic nanocarriers may be formulated by the methods described in International Pub Nos. WO2010005740, WO2010030763 and WO201213501 and US Pub. Nos. US20110262491, US20100104645, US20100087337 and US2012024422, the contents of each of which are herein incorporated by reference in their entirety. In another embodiment, the synthetic nanocarrier formulations may be lyophilized by methods described in International Pub. No. WO2011072218 and U.S. Pat. No. 8,211,473; the contents of each of which are herein incorporated by reference in their entirety.

In one embodiment, the synthetic nanocarriers may contain reactive groups to release the saRNA described herein (see International Pub. No. WO20120952552 and US Pub No. US20120171229, the contents of each of which are herein incorporated by reference in their entirety).

In one embodiment, the synthetic nanocarriers may be formulated for targeted release. In one embodiment, the synthetic nanocarrier may be formulated to release the saRNA at a specified pH and/or after a desired time interval. As a non-limiting example, the synthetic nanoparticle may be formulated to release the saRNA after 24 hours and/or at a pH of 4.5 (see International Pub. Nos. WO2010138193 and WO2010138194 and US Pub Nos. US20110020388 and US20110027217, the contents of each of which is herein incorporated by reference in their entireties).

In one embodiment, the synthetic nanocarriers may be formulated for controlled and/or sustained release of the saRNA described herein. As a non-limiting example, the synthetic nanocarriers for sustained release may be formulated by methods known in the art, described herein and/or as described in International Pub No. WO2010138192 and US Pub No. 20100303850, the contents each of which is herein incorporated by reference in their entirety.

In one embodiment, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; the contents of which are herein incorporated by reference in its entirety.

In one embodiment, the saRNA of the present invention may be formulated in a modular composition such as described in U.S. Pat. No. 8,575,123 to Manoharan et al., the contents of which are herein incorporated by reference in their entirety. As a non-limiting example, the modular composition may comprise a nucleic acid, e.g., the saRNA of the present invention, at least one endosomolytic component, and at least one targeting ligand. The modular composition may have a formula such as any formula described in U.S. Pat. No. 8,575,123 to Manoharan et al., the contents of which are herein incorporated by reference in their entirety.

In one embodiment, the saRNA of the present invention may be encapsulated in the lipid formulation to form a stable nucleic acid-lipid particle (SNALP) such as described in U.S. Pat. No. 8,546,554 to de Fougerolles et al., the contents of which are incorporated here by reference in their entirety. The lipid may be cationic or non-cationic. In one non-limiting example, the lipid to nucleic acid ratio (mass/mass ratio) (e.g., lipid to saRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1, or 5:1, 6:1, 7:1, 8:1, 9:1, 10:1, or 11:1. In another example, the SNALP includes 40% 2,2-Dilinoleyl-4-dimethylaminoethyl-[1,3]-dioxolane (Lipid A), 10% dioleoylphosphatidylcholine (DSPC), 40% cholesterol, 10% polyethyleneglycol (PEG)-C-DOMG (mole percent) with a particle size of 63.0±20 nm and a 0.027 nucleic acid/lipid ratio. In another embodiment, the saRNA of the present invention may be formulated with a nucleic acid-lipid particle comprising an endosomal membrane destabilizer as disclosed in U.S. Pat. No. 7,189,705 to Lam et al., the contents of which are incorporated herein by reference in their entirety. As a non-limiting example, the endosomal membrane destabilizer may be a $Ca^{2+}$ ion.

In one embodiment, the saRNA of the present invention may be formulated with formulated lipid particles (FLiPs) disclosed in U.S. Pat. No. 8,148,344 to Akinc et al., the contents of which are herein incorporated by reference in their entirety. Akinc et al. teach that FLiPs may comprise at least one of a single or double-stranded oligonucleotide, where the oligonucleotide has been conjugated to a lipophile and at least one of an emulsion or liposome to which the conjugated oligonucleotide has been aggregated, admixed or associated. These particles have surprisingly been shown to effectively deliver oligonucleotides to heart, lung and muscle disclosed in U.S. Pat. No. 8,148,344 to Akinc et al., the contents of which are herein incorporated by reference in their entirety.

In one embodiment, the saRNA of the present invention may be delivered to a cell using a composition comprising an expression vector in a lipid formulation as described in U.S. Pat. No. 6,086,913 to Tam et al., the contents of which are incorporated herein by reference in their entirety. The composition disclosed by Tam is serum-stable and comprises an expression vector comprising first and second inverted repeated sequences from an adeno associated virus (AAV), a rep gene from AAV, and a nucleic acid fragment. The expression vector in Tam is complexed with lipids.

In one embodiment, the saRNA of the present invention may be formulated with a lipid formulation disclosed in US 20120270921 to de Fougerolles et al., the contents of which are incorporated herein by reference in their entirety. In one non-limiting example, the lipid formulation may include a cationic lipid having the formula A described in US 20120270921, the contents of which are herein incorporated by reference in its entirety. In another non-limiting example, the compositions of exemplary nucleic acid-lipid particles disclosed in Table A of US 20120270921, the contents of which are incorporated herein by reference in their entirety, may be used with the saRNA of the present invention.

In one embodiment, the saRNA of the present invention may be fully encapsulated in a lipid particle disclosed in US 20120276207 to Maurer et al., the contents of which are incorporated herein by reference in their entirety. The particles may comprise a lipid composition comprising preformed lipid vesicles, a charged therapeutic agent, and a destabilizing agent to form a mixture of preformed vesicles and therapeutic agent in a destabilizing solvent, wherein the destabilizing solvent is effective to destabilize the membrane of the preformed lipid vesicles without disrupting the vesicles.

In one embodiment, the saRNA of the present invention may be formulated with a conjugated lipid. In a non-limiting example, the conjugated lipid may have a formula such as described in US 20120264810 to Lin et al., the contents of which are incorporated herein by reference in their entirety. The conjugate lipid may form a lipid particle which further comprises a cationic lipid, a neutral lipid, and a lipid capable of reducing aggregation.

In one embodiment, the saRNA of the present invention may be formulated in a neutral liposomal formulation such as disclosed in US 20120244207 to Fitzgerald et al., the contents of which are incorporated herein by reference in their entirety. The phrase "neutral liposomal formulation" refers to a liposomal formulation with a near neutral or neutral surface charge at a physiological pH. Physiological pH can be, e.g., about 7.0 to about 7.5, or, e.g., about 7.5, or, e.g., 7.0, 7.1, 7.2, 7.3, 7.4, or 7.5, or, e.g., 7.3, or, e.g., 7.4. An example of a neutral liposomal formulation is an ionizable lipid nanoparticle (iLNP). A neutral liposomal formulation can include an ionizable cationic lipid, e.g., DLin-KC2-DMA.

In one embodiment, the saRNA of the present invention may be formulated with a charged lipid or an amino lipid. As used herein, the term "charged lipid" is meant to include those lipids having one or two fatty acyl or fatty alkyl chains and a quaternary amino head group. The quaternary amine carries a permanent positive charge. The head group can optionally include an ionizable group, such as a primary, secondary, or tertiary amine that may be protonated at physiological pH. The presence of the quaternary amine can alter the pKa of the ionizable group relative to the pKa of the group in a structurally similar compound that lacks the quaternary amine (e.g., the quaternary amine is replaced by a tertiary amine) In some embodiments, a charged lipid is referred to as an "amino lipid." In a non-limiting example, the amino lipid may be any amino lipid described in US20110256175 to Hope et al., the contents of which are incorporated herein by reference in their entirety. For example, the amino lipids may have the structure disclosed in Tables 3-7 of Hope, such as structure (II), DLin-K-C2-DMA, DLin-K2-DMA, DLin-K6-DMA, etc. The resulting pharmaceutical preparations may be lyophilized according to Hope. In another non-limiting example, the amino lipids may be any amino lipid described in US 20110117125 to Hope et al., the contents of which are incorporated herein by reference in their entirety, such as a lipid of structure (I), DLin-K-DMA, DLin-C-DAP, DLin-DAC, DLin-MA, DLin-S-DMA, etc. In another non-limiting example, the amino lipid may have the structure (I), (II), (III), or (IV), or 4-(R)-DLin-K-DMA (VI), 4-(S)-DLin-K-DMA (V) as described in WO2009132131 to Manoharan et al., the contents of which are incorporated herein by reference in their entirety. In another non-limiting example, the charged lipid used in any of the formulations described herein may be any charged lipid described in EP2509636 to Manoharan et al., the contents of which are incorporated herein by reference in their entirety.

In one embodiment, the saRNA of the present invention may be formulated with an association complex containing lipids, liposomes, or lipoplexes. In a non-limiting example, the association complex comprises one or more compounds each having a structure defined by formula (I), a PEG-lipid having a structure defined by formula (XV), a steroid and a nucleic acid disclosed in U.S. Pat. No. 8,034,376 to Manoharan et al., the contents of which are incorporated herein by reference in their entirety. The saRNA may be formulated with any association complex described in U.S. Pat. No. 8,034,376, the contents of which are herein incorporated by reference in its entirety.

In one embodiment, the saRNA of the present invention may be formulated with reverse head group lipids. As a non-limiting example, the saRNA may be formulated with a zwitterionic lipid comprising a headgroup wherein the positive charge is located near the acyl chain region and the negative charge is located at the distal end of the head group, such as a lipid having structure (A) or structure (I) described in WO2011056682 to Leung et al., the contents of which are incorporated herein by reference in their entirety.

In one embodiment, the saRNA of the present invention may be formulated in a lipid bilayer carrier. As a non-limiting example, the saRNA may be combined with a lipid-detergent mixture comprising a lipid mixture of an aggregation-preventing agent in an amount of about 5 mol % to about 20 mol %, a cationic lipid in an amount of about 0.5 mol % to about 50 mol %, and a fusogenic lipid and a detergent, to provide a nucleic acid-lipid-detergent mixture; and then dialyzing the nucleic acid-lipid-detergent mixture against a buffered salt solution to remove the detergent and to encapsulate the nucleic acid in a lipid bilayer carrier and provide a lipid bilayer-nucleic acid composition, wherein the buffered salt solution has an ionic strength sufficient to encapsulate of from about 40% to about 80% of the nucleic acid, described in WO1999018933 to Cullis et al., the contents of which are incorporated herein by reference in their entirety.

In one embodiment, the saRNA of the present invention may be formulated in a nucleic acid-lipid particle capable of selectively targeting the saRNA to a heart, liver, or tumor tissue site. For example, the nucleic acid-lipid particle may comprise (a) a nucleic acid; (b) 1.0 mole % to 45 mole % of a cationic lipid; (c) 0.0 mole % to 90 mole % of another lipid; (d) 1.0 mole % to 10 mole % of a bilayer stabilizing component; (e) 0.0 mole % to 60 mole % cholesterol; and (f) 0.0 mole % to 10 mole % of cationic polymer lipid as described in EP1328254 to Cullis et al., the contents of which are incorporated herein by reference in their entirety. Cullis teaches that varying the amount of each of the cationic lipid, bilayer stabilizing component, another lipid, cholesterol, and cationic polymer lipid can impart tissue selectivity for heart, liver, or tumor tissue site, thereby identifying a nucleic acid-lipid particle capable of selectively targeting a nucleic acid to the heart, liver, or tumor tissue site.

Polymers, Biodegradable Nanoparticles, and Core-Shell Nanoparticles

The saRNA of the invention can be formulated using natural and/or synthetic polymers. Non-limiting examples of polymers which may be used for delivery include, but are not limited to, DYNAMIC POLYCONJUGATE® (Arrowhead Research Corp., Pasadena, Calif.) formulations from MIRUS® Bio (Madison, Wis.) and Roche Madison (Madison, Wis.), PHASERX™ polymer formulations such as, without limitation, SMARTT POLYMER TECHNOLOGY™ (PHASERX®, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly(lactic-co-glycolic acid) (PLGA) polymers. RONDEL™ (RNAi/Oligonucleotide Nanoparticle Delivery) polymers (Arrowhead Research Corporation, Pasadena, Calif.) and pH responsive co-block polymers such as, but not limited to, PHASERX® (Seattle, Wash.).

A non-limiting example of chitosan formulation includes a core of positively charged chitosan and an outer portion of negatively charged substrate (U.S. Pub. No. 20120258176; herein incorporated by reference in its entirety). Chitosan includes, but is not limited to N-trimethyl chitosan, mono-N-carboxymethyl chitosan (MCC), N-palmitoyl chitosan (NPCS), EDTA-chitosan, low molecular weight chitosan, chitosan derivatives, or combinations thereof.

In one embodiment, the polymers used in the present invention have undergone processing to reduce and/or inhibit the attachment of unwanted substances such as, but not limited to, bacteria, to the surface of the polymer. The polymer may be processed by methods known and/or described in the art and/or described in International Pub. No. WO2012150467, herein incorporated by reference in its entirety.

A non-limiting example of PLGA formulations include, but are not limited to, PLGA injectable depots (e.g., ELIGARD® which is formed by dissolving PLGA in 66% N-methyl-2-pyrrolidone (NMP) and the remainder being aqueous solvent and leuprolide. Once injected, the PLGA and leuprolide peptide precipitates into the subcutaneous space).

Many of these polymer approaches have demonstrated efficacy in delivering oligonucleotides in vivo into the cell cytoplasm (reviewed in de Fougerolles *Hum Gene Ther.* 2008 19:125-132; herein incorporated by reference in its entirety). Two polymer approaches that have yielded robust in vivo delivery of nucleic acids, in this case with small interfering RNA (siRNA), are dynamic polyconjugates and cyclodextrin-based nanoparticles. The first of these delivery approaches uses dynamic polyconjugates and has been shown in vivo in mice to effectively deliver siRNA and silence endogenous target mRNA in hepatocytes (Rozema et al., Proc Natl Acad Sci USA. 2007 104:12982-12887; herein incorporated by reference in its entirety). This particular approach is a multicomponent polymer system whose key features include a membrane-active polymer to which nucleic acid, in this case siRNA, is covalently coupled via a disulfide bond and where both PEG (for charge masking) and N-acetylgalactosamine (for hepatocyte targeting) groups are linked via pH-sensitive bonds (Rozema et al., Proc Natl Acad Sci USA. 2007 104:12982-12887; herein incorporated by reference in its entirety). On binding to the hepatocyte and entry into the endosome, the polymer complex disassembles in the low-pH environment, with the polymer exposing its positive charge, leading to endosomal escape and cytoplasmic release of the siRNA from the polymer. Through replacement of the N-acetylgalactosamine group with a mannose group, it was shown one could alter targeting from asialoglycoprotein receptor-expressing hepatocytes to sinusoidal endothelium and Kupffer cells. Another polymer approach involves using transferrin-targeted cyclodextrin-containing polycation nanoparticles. These nanoparticles have demonstrated targeted silencing of the EWS-FLI1 gene product in transferrin receptor-expressing Ewing's sarcoma tumor cells (Hu-Lieskovan et al., Cancer Res. 2005 65: 8984-8982; herein incorporated by reference in its entirety) and siRNA formulated in these nanoparticles was well tolerated in non-human primates (Heidel et al., Proc Natl Acad Sci USA 2007 104:5715-21; herein incorporated by reference in its entirety). Both of these delivery strategies incorporate rational approaches using both targeted delivery and endosomal escape mechanisms.

The polymer formulation can permit the sustained or delayed release of saRNA (e.g., following intramuscular or subcutaneous injection). The altered release profile for the saRNA can result in, for example, translation of an encoded protein over an extended period of time. Biodegradable polymers have been previously used to protect nucleic acids from degradation and been shown to result in sustained release of payloads in vivo (Rozema et al., Proc Natl Acad Sci USA. 2007 104:12982-12887; Sullivan et al., Expert Opin Drug Deliv. 2010 7:1433-1446; Convertine et al., Biomacromolecules. 2010 Oct. 1; Chu et al., Acc Chem Res. 2012 Jan. 13; Manganiello et al., Biomaterials. 2012 33:2301-2309; Benoit et al., Biomacromolecules. 2011 12:2708-2714; Singha et al., Nucleic Acid Ther. 2011 2:133-147; de Fougerolles Hum Gene Ther. 2008 19:125-132; Schaffert and Wagner, Gene Ther. 2008 16:1131-1138; Chaturvedi et al., Expert Opin Drug Deliv. 2011 8:1455-1468; Davis, Mol Pharm. 2009 6:659-668; Davis, Nature 2010 464:1067-1070; each of which is herein incorporated by reference in its entirety).

In one embodiment, the pharmaceutical compositions may be sustained release formulations. In a further embodiment, the sustained release formulations may be for subcutaneous delivery. Sustained release formulations may include, but are not limited to, PLGA microspheres, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

As a non-limiting example saRNA may be formulated in PLGA microspheres by preparing the PLGA microspheres with tunable release rates (e.g., days and weeks) and encapsulating the saRNA in the PLGA microspheres while maintaining the integrity of the saRNA during the encapsulation process. EVAc are non-biodegradable, biocompatible polymers which are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C. PEG-based surgical sealants comprise two synthetic PEG components mixed in a delivery device which can be prepared in one minute, seals in 3 minutes and is reabsorbed within 30 days. GELSITE® and natural polymers are capable of in-situ gelation at the site of administration. They have been shown to interact with protein and peptide therapeutic candidates through ionic interaction to provide a stabilizing effect.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714; Rozema et al., Proc Natl Acad Sci USA. 2007 104:12982-12887; Davis, Mol Pharm. 2009 6:659-668; Davis, Nature 2010 464:1067-1070; each of which is herein incorporated by reference in its entirety).

The saRNA of the invention may be formulated with or in a polymeric compound. The polymer may include at least one polymer such as, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly (alkylene imines), a polyamine derivative, a modified poloxamer, a biodegradable polymer, elastic biodegradable polymer, biodegradable block copolymer, biodegradable random copolymer, biodegradable polyester copolymer, biodegradable polyester block copolymer, biodegradable polyester block random copolymer, multiblock copolymers, linear biodegradable copolymer, poly[α-(4-aminobutyl)-L-glycolic acid] (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), acrylic polymers, amine-containing polymers, dextran polymers, dextran polymer derivatives or combinations thereof.

As a non-limiting example, the saRNA of the invention may be formulated with the polymeric compound of PEG grafted with PLL as described in U.S. Pat. No. 6,177,274; herein incorporated by reference in its entirety. The formulation may be used for transfecting cells in vitro or for in vivo delivery of the saRNA. In another example, the saRNA may be suspended in a solution or medium with a cationic polymer, in a dry pharmaceutical composition or in a solution that is capable of being dried as described in U.S. Pub. Nos. 20090042829 and 20090042825; each of which are herein incorporated by reference in their entireties.

As another non-limiting example the saRNA of the invention may be formulated with a PLGA-PEG block copolymer (see US Pub. No. US20120004293 and U.S. Pat. No. 8,236,330, herein incorporated by reference in their entireties) or PLGA-PEG-PLGA block copolymers (See U.S. Pat. No. 6,004,573, herein incorporated by reference in its entirety). As a non-limiting example, the saRNA of the invention may be formulated with a diblock copolymer of PEG and PLA or PEG and PLGA (see U.S. Pat. No. 8,246,968, herein incorporated by reference in its entirety).

A polyamine derivative may be used to deliver nucleic acids or to treat and/or prevent a disease or to be included in an implantable or injectable device (U.S. Pub. No. 20100260817 herein incorporated by reference in its entirety). As a non-limiting example, a pharmaceutical composition may include the saRNA and the polyamine derivative described in U.S. Pub. No. 20100260817 (the contents of which are incorporated herein by reference in its entirety. As a non-limiting example the saRNA of the present invention may be delivered using a polyamide polymer such as, but not limited to, a polymer comprising a 1,3-dipolar addition polymer prepared by combining a carbohydrate diazide monomer with a dilkyne unite comprising oligoamines (U.S. Pat. No. 8,236,280; herein incorporated by reference in its entirety).

In one embodiment, the saRNA of the present invention may be formulated with at least one polymer and/or derivatives thereof described in International Publication Nos. WO2011115862, WO2012082574 and WO2012068187 and U.S. Pub. No. 20120283427, the contents of each of which are herein incorporated by reference in their entireties. In another embodiment, the saRNA of the present invention may be formulated with a polymer of formula Z as described in WO2011115862, herein incorporated by reference in its entirety. In yet another embodiment, the saRNA may be formulated with a polymer of formula Z, Z' or Z" as described in International Pub. Nos. WO2012082574 or WO2012068187 and U.S. Pub. No. 2012028342, the contents of each of which are herein incorporated by reference in their entireties. The polymers formulated with the saRNA of the present invention may be synthesized by the methods described in International Pub. Nos. WO2012082574 or WO2012068187, the contents of each of which are herein incorporated by reference in their entireties.

The saRNA of the invention may be formulated with at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

Formulations of saRNA of the invention may include at least one amine-containing polymer such as, but not limited to polylysine, polyethylene imine, poly(amidoamine) dendrimers or combinations thereof.

For example, the saRNA of the invention may be formulated in a pharmaceutical compound including a poly(alkylene imine), a biodegradable cationic lipopolymer, a biodegradable block copolymer, a biodegradable polymer, or a biodegradable random copolymer, a biodegradable polyester block copolymer, a biodegradable polyester polymer, a biodegradable polyester random copolymer, a linear biodegradable copolymer, PAGA, a biodegradable cross-linked cationic multi-block copolymer or combinations thereof. The biodegradable cationic lipopolymer may be made by methods known in the art and/or described in U.S. Pat. No. 6,696,038, U.S. App. Nos. 20030073619 and 20040142474 each of which is herein incorporated by reference in their entireties. The poly(alkylene imine) may be made using methods known in the art and/or as described in U.S. Pub. No. 20100004315, herein incorporated by reference in its entirety. The biodegradable polymer, biodegradable block copolymer, the biodegradable random copolymer, biodegradable polyester block copolymer, biodegradable polyester polymer, or biodegradable polyester random copolymer may be made using methods known in the art and/or as described in U.S. Pat. Nos. 6,517,869 and 6,267,987, the contents of which are each incorporated herein by reference in their entirety. The linear biodegradable copolymer may be made using methods known in the art and/or as described in U.S. Pat. No. 6,652,886. The PAGA polymer may be made using methods known in the art and/or as described in U.S. Pat. No. 6,217,912 herein incorporated by reference in its entirety. The PAGA polymer may be copolymerized to form a copolymer or block copolymer with polymers such as but not limited to, poly-L-lysine, polyargine, polyornithine, histones, avidin, protamines, polylactides and poly(lactide-co-glycolides). The biodegradable cross-linked cationic multi-block copolymers may be made my methods known in the art and/or as described in U.S. Pat. No. 8,057,821 or U.S. Pub. No. 2012009145 each of which are herein incorporated by reference in their entireties. For example, the multi-block copolymers may be synthesized using linear polyethyleneimine (LPEI) blocks which have distinct patterns as compared to branched polyethyleneimines. Further, the composition or pharmaceutical composition may be made by the methods known in the art, described herein, or as described in U.S. Pub. No. 20100004315 or U.S. Pat. Nos. 6,267,987 and 6,217,912 each of which are herein incorporated by reference in their entireties.

The saRNA of the invention may be formulated with at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

The saRNA of the invention may be formulated with at least one crosslinkable polyester. Crosslinkable polyesters include those known in the art and described in US Pub. No. 20120269761, herein incorporated by reference in its entirety.

In one embodiment, the polymers described herein may be conjugated to a lipid-terminating PEG. As a non-limiting example, PLGA may be conjugated to a lipid-terminating PEG forming PLGA-DSPE-PEG. As another non-limiting example, PEG conjugates for use with the present invention are described in International Publication No. WO2008103276, herein incorporated by reference in its entirety. The polymers may be conjugated using a ligand conjugate such as, but not limited to, the conjugates described in U.S. Pat. No. 8,273,363, herein incorporated by reference in its entirety.

In one embodiment, the saRNA described herein may be conjugated with another compound. Non-limiting examples of conjugates are described in U.S. Pat. Nos. 7,964,578 and 7,833,992, each of which are herein incorporated by reference in their entireties. In another embodiment, saRNA of the present invention may be conjugated with conjugates of formula 1-122 as described in U.S. Pat. Nos. 7,964,578 and 7,833,992, each of which are herein incorporated by reference in their entireties. The saRNA described herein may be conjugated with a metal such as, but not limited to, gold. (See e.g., Giljohann et al. Journ. Amer. Chem. Soc. 2009 131(6): 2072-2073; herein incorporated by reference in its entirety). In another embodiment, the saRNA described herein may be conjugated and/or encapsulated in gold-nanoparticles. (International Pub. No. WO201216269 and U.S. Pub. No. 20120302940; each of which is herein incorporated by reference in its entirety).

As described in U.S. Pub. No. 20100004313, herein incorporated by reference in its entirety, a gene delivery composition may include a nucleotide sequence and a poloxamer. For example, the saRNA of the present invention may be used in a gene delivery composition with the poloxamer described in U.S. Pub. No. 20100004313.

In one embodiment, the polymer formulation of the present invention may be stabilized by contacting the polymer formulation, which may include a cationic carrier, with a cationic lipopolymer which may be covalently linked to cholesterol and polyethylene glycol groups. The polymer formulation may be contacted with a cationic lipopolymer using the methods described in U.S. Pub. No. 20090042829 herein incorporated by reference in its entirety.

The cationic carrier may include, but is not limited to, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, 1,2-Dioleoyl-3-Trimethylammonium-Propane (DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), 3B—[N—(N',N'-Dimethylaminoethane)-carbamoyl]Cholesterol Hydrochloride (DC-Cholesterol HCl) diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride DODAC) and combinations thereof.

The saRNA of the invention may be formulated in a polyplex of one or more polymers (U.S. Pub. No. 20120237565 and 20120270927; each of which is herein incorporated by reference in its entirety). In one embodiment, the polyplex comprises two or more cationic polymers. The cationic polymer may comprise a poly(ethylene imine) (PEI) such as linear PEI.

The saRNA of the invention can also be formulated as a nanoparticle using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so to delivery of the saRNA may be enhanced (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in its entirety). As a non-limiting example, the nanoparticle may comprise a plurality of polymers such as, but not limited to hydrophilic-hydrophobic polymers (e.g., PEG-PLGA), hydrophobic polymers (e.g., PEG) and/or hydrophilic polymers (International Pub. No. WO20120225129; herein incorporated by reference in its entirety).

Biodegradable calcium phosphate nanoparticles in combination with lipids and/or polymers may be used to deliver saRNA in vivo. In one embodiment, a lipid coated calcium phosphate nanoparticle, which may also contain a targeting ligand such as anisamide, may be used to deliver the saRNA of the present invention. For example, to effectively deliver siRNA in a mouse metastatic lung model a lipid coated calcium phosphate nanoparticle was used (Li et al., J Contr Rel. 2010 142: 416-421; Li et al., J Contr Rel. 2012 158:108-114; Yang et al., Mol Ther. 2012 20:609-615; herein incorporated by reference in its entirety). This delivery system combines both a targeted nanoparticle and a component to enhance the endosomal escape, calcium phosphate, in order to improve delivery of the siRNA.

In one embodiment, calcium phosphate with a PEG-polyanion block copolymer may be used to delivery saRNA (Kazikawa et al., J Contr Rel. 2004 97:345-356; Kazikawa et al., J Contr Rel. 2006 111:368-370; herein incorporated by reference in its entirety).

In one embodiment, a PEG-charge-conversional polymer (Pitella et al., Biomaterials. 2011 32:3106-3114) may be used to form a nanoparticle to deliver the saRNA of the present invention. The PEG-charge-conversional polymer may improve upon the PEG-polyanion block copolymers by being cleaved into a polycation at acidic pH, thus enhancing endosomal escape.

The use of core-shell nanoparticles has additionally focused on a high-throughput approach to synthesize cationic cross-linked nanogel cores and various shells (Siegwart et al., Proc Natl Acad Sci USA. 2011 108:12996-13001). The complexation, delivery, and internalization of the polymeric nanoparticles can be precisely controlled by altering the chemical composition in both the core and shell components of the nanoparticle. For example, the core-shell nanoparticles may efficiently deliver saRNA to mouse hepatocytes after they covalently attach cholesterol to the nanoparticle.

In one embodiment, a hollow lipid core comprising a middle PLGA layer and an outer neutral lipid layer containing PEG may be used to delivery of the saRNA of the present invention. As a non-limiting example, in mice bearing a luciferase-expressing tumor, it was determined that the lipid-polymer-lipid hybrid nanoparticle significantly suppressed luciferase expression, as compared to a conventional lipoplex (Shi et al, Angew Chem Int Ed. 2011 50:7027-7031; herein incorporated by reference in its entirety).

In one embodiment, the lipid nanoparticles may comprise a core of the saRNA disclosed herein and a polymer shell. The polymer shell may be any of the polymers described herein and are known in the art. In an additional embodiment, the polymer shell may be used to protect the modified nucleic acids in the core.

Core-shell nanoparticles for use with the saRNA of the present invention may be formed by the methods described in U.S. Pat. No. 8,313,777 herein incorporated by reference in its entirety.

In one embodiment, the core-shell nanoparticles may comprise a core of the saRNA disclosed herein and a polymer shell. The polymer shell may be any of the polymers described herein and are known in the art. In an additional embodiment, the polymer shell may be used to protect the saRNA in the core. As a non-limiting example, the core-shell nanoparticle may be used to treat an eye disease or disorder (See e.g. US Publication No. 20120321719, herein incorporated by reference in its entirety).

In one embodiment, the polymer used with the formulations described herein may be a modified polymer (such as, but not limited to, a modified polyacetal) as described in International Publication No. WO2011120053, herein incorporated by reference in its entirety.

Delivery

The present disclosure encompasses the delivery of saRNA for any of therapeutic, prophylactic, pharmaceutical, diagnostic or imaging by any appropriate route taking into consideration likely advances in the sciences of drug delivery. Delivery may be naked or formulated.

The saRNA of the present invention may be delivered to a cell naked. As used herein in, "naked" refers to delivering saRNA free from agents which promote transfection. For example, the saRNA delivered to the cell may contain no modifications. The naked saRNA may be delivered to the cell using routes of administration known in the art and described herein.

The saRNA of the present invention may be formulated, using the methods described herein. The formulations may contain saRNA which may be modified and/or unmodified. The formulations may further include, but are not limited to, cell penetration agents, a pharmaceutically acceptable carrier, a delivery agent, a bioerodible or biocompatible polymer, a solvent, and a sustained-release delivery depot. The formulated saRNA may be delivered to the cell using routes of administration known in the art and described herein.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like. The saRNA of the present invention may also be cloned into a retroviral replicating vector (RRV) and transduced to cells.

Administration

The saRNA of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Routes of administration disclosed in International Publication WO 2013/090648 filed Dec. 14, 2012, the contents of which are incorporated herein by reference in their entirety, may be used to administer the saRNA of the present invention.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous). Liquid dosage forms, injectable preparations, pulmonary forms, and solid dosage forms described in International Publication WO 2013/090648 filed Dec. 14, 2012, the contents of which are incorporated herein by reference in their entirety may be used as dosage forms for the saRNA of the present invention.

III. Methods of Use

One aspect of the present invention provides methods of using saRNA of the present invention and pharmaceutical compositions comprising the saRNA and at least one pharmaceutically acceptable carrier. The saRNA of the present invention modulates the expression of its target gene. In one embodiment is provided a method of regulating the expression of a target gene in vitro and/or in vivo comprising administering the saRNA of the present invention. In one embodiment, the expression of the target gene is increased by at least 5, 10, 20, 30, 40%, or at least 45, 50, 55, 60, 65, 70, 75%, or at least 80% in the presence of the saRNA of the present invention compared to the expression of the target gene in the absence of the saRNA of the present invention. In a further embodiment, the expression of the target gene is increased by a factor of at least 2, 3, 4, 5, 6, 7, 8, 9, 10, or by a factor of at least 15, 20, 25, 30, 35, 40, 45, 50, or by a factor of at least 60, 70, 80, 90, 100, in the presence of the saRNA of the present invention compared to the expression of the target gene in the absence of the saRNA of the present invention.

SIRT1 Gene

One aspect of the present application provides a method of modulating the expression of SIRT1 gene comprising administering SIRT1-saRNA of the present invention. In one embodiment, the expression of SIRT1 gene is increased by at least 20, 30, 40%, or at least 45, 50, 55, 60, 65, 70, 75%, or at least 80% in the presence of the SIRT1-saRNA of the present invention compared to the expression of SIRT1 gene in the absence of the SIRT1-saRNA of the present invention. In a further embodiment, the expression of SIRT1 gene is increased by a factor of at least 2, 3, 4, 5, 6, 7, 8, 9, 10, or by a factor of at least 15, 20, 25, 30, 35, 40, 45, 50, or by a factor of at least 60, 70, 80, 90, 100, in the presence of the SIRT1-saRNA of the present invention compared to the expression of SIRT1 gene in the absence of the SIRT1-saRNA of the present invention. The modulation of the expression of SIRT1 gene may be reflected or determined by the change of SIRT1 mRNA levels.

SIRT1 gene encodes sirtuin 1 (SIRT1) protein, also known as NAD-dependent Deacetylase sirtuin-1, which is an enzyme that deacetylates proteins that contribute to cellular regulation. SIRT1 protein is associated with insulin sensitivity and type 2 diabetes (Sun et al., *Cell Metab.*, vol. 6 (4):307 (2007), the contents of which are incorporated herein by reference in their entirety).

In some embodiments, provided is a method of modulating SIRT1 protein levels comprising administering SIRT1-saRNAs of the present invention. In one embodiment, the expression of the SIRT1 gene, such as the SIRT1 mRNA and/or SIRT1 protein level, is increased by at least 20, 30, 40%, or at least 45, 50, 55, 60, 65, 70, 75%, or at least 80% in the presence of the SIRT1-saRNA of the present invention compared to the expression of the SIRT1 gene in the absence of the SIRT1-saRNA of the present invention. In a further embodiment, the expression of the SIRT1 gene, such as the SIRT1 mRNA and/or SIRT1 protein level, is increased by a factor of at least 2, 3, 4, 5, 6, 7, 8, 9, 10, or by a factor of at least 15, 20, 25, 30, 35, 40, 45, 50, or by a factor of at least 60, 70, 80, 90, 100, in the presence of the SIRT1-saRNA of the present invention compared to the expression of the SIRT1 gene in the absence of the SIRT1-saRNA of the present invention.

In some embodiments, provided is a method of improving cellular metabolism in all organs of a subject, such as liver, pancreas, heart, kidney, and/or brain, comprising administering SIRT1-saRNAs of the present invention.

SIRT1-saRNAs of the present invention may be used to prevent or treat diseases or disorders associated with SIRT1. In some embodiments, SIRT1-saRNA of the present invention is used to prevent or treat diseases such as non-alcoholic fatty liver disease (NASH), type II diabetes (T2D), dyslipidaemia, obesity, type I diabetes (TID), high blood pressure, arrhythmias, glomerulonephritis, and/or neurodegenerative diseases.

IV. Kits and Devices

Kits

The invention provides a variety of kits for conveniently and/or effectively carrying out methods of the present invention. Typically, kits will comprise sufficient amounts and/or numbers of components to allow a user to perform multiple treatments of a subject(s) and/or to perform multiple experiments.

In one embodiment, the present invention provides kits for regulate the expression of genes in vitro or in vivo, comprising saRNA of the present invention or a combination of saRNA of the present invention, saRNA modulating other genes, siRNAs, miRNAs or other oligonucleotide molecules.

The kit may further comprise packaging and instructions and/or a delivery agent to form a formulation composition. The delivery agent may comprise a saline, a buffered solution, a lipidoid, a dendrimer or any delivery agent disclosed herein.

In one non-limiting example, the buffer solution may include sodium chloride, calcium chloride, phosphate and/or EDTA. In another non-limiting example, the buffer solution may include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See U.S. Pub. No. 20120258046; herein incorporated by reference in its entirety). In yet another non-limiting example, the buffer solutions may be precipitated or it may be lyophilized. The amount of each component may be varied to enable consistent, reproducible higher concentration saline or simple buffer formulations. The components may also be varied in order to increase the stability of saRNA in the buffer solution over a period of time and/or under a variety of conditions.

Devices

The present invention provides for devices which may incorporate saRNA of the present invention. These devices contain in a stable formulation available to be immediately delivered to a subject in need thereof, such as a human patient.

Non-limiting examples of the devices include a pump, a catheter, a needle, a transdermal patch, a pressurized olfactory delivery device, iontophoresis devices, multi-layered microfluidic devices. The devices may be employed to deliver saRNA of the present invention according to single, multi- or split-dosing regiments. The devices may be employed to deliver saRNA of the present invention across biological tissue, intradermal, subcutaneously, or intramuscularly. More examples of devices suitable for delivering oligonucleotides are disclosed in International Publication WO 2013/090648 filed Dec. 14, 2012, the contents of which are incorporated herein by reference in their entirety.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

About: As used herein, the term "about" means +/−10% of the recited value.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently close together such that a combinatorial (e.g., a synergistic) effect is achieved.

Amino acid: As used herein, the terms "amino acid" and "amino acids" refer to all naturally occurring L-alpha-amino acids. The amino acids are identified by either the one-letter or three-letter designations as follows: aspartic acid (Asp: D), isoleucine (Ile:I), threonine (Thr:T), leucine (Leu:L), serine (Ser:S), tyrosine (Tyr:Y), glutamic acid (Glu:E), phenylalanine (Phe:F), proline (Pro:P), histidine (His:H), glycine (Gly:G), lysine (Lys:K), alanine (Ala:A), arginine (Arg:R), cysteine (Cys:C), tryptophan (Trp:W), valine (Val: V), glutamine (Gln:Q) methionine (Met:M), asparagines (Asn:N), where the amino acid is listed first followed parenthetically by the three and one letter codes, respectively.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunction or Bifunctional: As used herein, the terms "bifunction" and "bifunctional" refers to any substance, molecule or moiety which is capable of or maintains at least two functions. The functions may affect the same outcome or a different outcome. The structure that produces the function may be the same or different. For example, bifunctional saRNA of the present invention may comprise a cytotoxic peptide (a first function) while those nucleosides which comprise the saRNA are, in and of themselves, cytotoxic (second function).

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, the saRNA of the present invention may be considered biologically active if even a portion of the saRNA is biologically active or mimics an activity considered biologically relevant.

Cancer: As used herein, the term "cancer" in an individual refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an individual, or may circulate in the blood stream as independent cells, such as leukemic cells.

Cell growth: As used herein, the term "cell growth" is principally associated with growth in cell numbers, which occurs by means of cell reproduction (i.e. proliferation) when the rate of the latter is greater than the rate of cell death (e.g. by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

Cell type: As used herein, the term "cell type" refers to a cell from a given source (e.g., a tissue, organ) or a cell in a given state of differentiation, or a cell associated with a given pathology or genetic makeup.

Chromosome: As used herein, the term "chromosome" refers to an organized structure of DNA and protein found in cells.

Complementary: As used herein, the term "complementary" as it relates to nucleic acids refers to hybridization or base pairing between nucleotides or nucleic acids, such as, for example, between the two strands of a double-stranded DNA molecule or between an oligonucleotide probe and a target are complementary.

Condition: As used herein, the term "condition" refers to the status of any cell, organ, organ system or organism. Conditions may reflect a disease state or simply the physiologic presentation or situation of an entity. Conditions may be characterized as phenotypic conditions such as the macroscopic presentation of a disease or genotypic conditions such as the underlying gene or protein expression profiles associated with the condition. Conditions may be benign or malignant.

Controlled Release: As used herein, the term "controlled release" refers to a pharmaceutical composition or compound release profile that conforms to a particular pattern of release to effect a therapeutic outcome.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a saRNA of the present invention to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the oligonucleotides disclosed herein. They may be within the nucleotides or located at the 5' or 3' terminus.

Encapsulate: As used herein, the term "encapsulate" means to enclose, surround or encase.

Engineered: As used herein, embodiments of the invention are "engineered" when they are designed to have a feature or property, whether structural or chemical, that varies from a starting point, wild type or native molecule.

Equivalent subject: As used herein, "equivalent subject" may be e.g. a subject of similar age, sex and health such as liver health or cancer stage, or the same subject prior to treatment according to the invention. The equivalent subject is "untreated" in that he does not receive treatment with a saRNA according to the invention. However, he may receive a conventional anti-cancer treatment, provided that the subject who is treated with the saRNA of the invention receives the same or equivalent conventional anti-cancer treatment.

Exosome: As used herein, "exosome" is a vesicle secreted by mammalian cells.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least one saRNA of the present invention and a delivery agent.

Fragment: A "fragment," as used herein, refers to a portion. For example, fragments of proteins may comprise polypeptides obtained by digesting full-length protein isolated from cultured cells. Fragments of oligonucleotides may comprise nucleotides, or regions of nucleotides.

Functional: As used herein, a "functional" biological molecule is a biological molecule in a form in which it exhibits a property and/or activity by which it is characterized.

Gene: As used herein, the term "gene" refers to a nucleic acid sequence that comprises control and most often coding sequences necessary for producing a polypeptide or precursor. Genes, however, may not be translated and instead code for regulatory or structural RNA molecules.

A gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions.

Gene expression: As used herein, the term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

Genome: The term "genome" is intended to include the entire DNA complement of an organism, including the nuclear DNA component, chromosomal or extrachromosomal DNA, as well as the cytoplasmic domain (e.g., mitochondrial DNA).

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

The term "hyperproliferative cell" may refer to any cell that is proliferating at a rate that is abnormally high in comparison to the proliferating rate of an equivalent healthy cell (which may be referred to as a "control"). An "equivalent healthy" cell is the normal, healthy counterpart of a cell. Thus, it is a cell of the same type, e.g. from the same organ, which performs the same functions(s) as the comparator cell. For example, proliferation of a hyperproliferative hepatocyte should be assessed by reference to a healthy hepatocyte, whereas proliferation of a hyperproliferative prostate cell should be assessed by reference to a healthy prostate cell.

By an "abnormally high" rate of proliferation, it is meant that the rate of proliferation of the hyperproliferative cells is increased by at least 20, 30, 40%, or at least 45, 50, 55, 60, 65, 70, 75%, or at least 80%, as compared to the proliferative rate of equivalent, healthy (non-hyperproliferative) cells. The "abnormally high" rate of proliferation may also refer to a rate that is increased by a factor of at least 2, 3, 4, 5, 6, 7, 8, 9, 10, or by a factor of at least 15, 20, 25, 30, 35, 40, 45, 50, or by a factor of at least 60, 70, 80, 90, 100, compared to the proliferative rate of equivalent, healthy cells.

Hyperproliferative disorder: As used herein, a "hyperproliferative disorder" may be any disorder which involves hyperproliferative cells as defined above. Examples of hyperproliferative disorders include neoplastic disorders such as cancer, psoriatic arthritis, rheumatoid arthritis, gastric hyperproliferative disorders such as inflammatory bowel disease, skin disorders including psoriasis, Reiter's syndrome, pityriasis rubra pilaris, and hyperproliferative variants of the disorders of keratinization.

The skilled person is fully aware of how to identify a hyperproliferative cell. The presence of hyperproliferative cells within an animal may be identifiable using scans such as X-rays, MRI or CT scans. The hyperproliferative cell may also be identified, or the proliferation of cells may be assayed, through the culturing of a sample in vitro using cell proliferation assays, such as MTT, XTT, MTS or WST-1 assays. Cell proliferation in vitro can also be determined using flow cytometry.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Altschul, S. F. et al., J. Molec. Biol., 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Label: The term "label" refers to a substance or a compound which is incorporated into an object so that the substance, compound or object may be detectable.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form saRNA conjugates, as well as to administer a payload, as described herein.

Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof. Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Metastasis: As used herein, the term "metastasis" means the process by which cancer invades and spreads from the place at which it first arose as a primary tumor to distant locations in the body. Metastasis also refers to cancers resulting from the spread of the primary tumor. For example, someone with breast cancer may show metastases in their lymph system, liver, bones or lungs.

Modified: As used herein "modified" refers to a changed state or structure of a molecule of the invention. Molecules may be modified in many ways including chemically, structurally, and functionally. In one embodiment, the saRNAs of the present invention are modified by the introduction of non-natural nucleosides and/or nucleotides.

Naturally occurring: As used herein, "naturally occurring" means existing in nature without artificial aid.

Nucleic acid: The term "nucleic acid" as used herein, refers to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being bound together, in the case of the polymers, via 5' to 3' linkages. The ribonucleotide and deoxyribonucleotide polymers may be single or double-stranded. However, linkages may include any of the linkages known in the art including, for example, nucleic acids comprising 5' to 3' linkages. The nucleotides may be naturally occurring or may be synthetically produced analogs that are capable of forming base-pair relationships with naturally occurring base pairs. Examples of non-naturally occurring bases that are capable of forming base-pairing relationships include, but are not limited to, aza and deaza pyrimidine analogs, aza and deaza purine analogs, and other heterocyclic base analogs, wherein one or more of the carbon and nitrogen atoms of the pyrimidine rings have been substituted by heteroatoms, e.g., oxygen, sulfur, selenium, phosphorus, and the like.

Patient: As used herein, "patient" refers to a subject who may seek or be in need of treatment, requires treatment, is receiving treatment, will receive treatment, or a subject who is under care by a trained professional for a particular disease or condition.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, *Pharmaceutical Salts: Properties, Selection*, and Use, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacologic effect: As used herein, a "pharmacologic effect" is a measurable biologic phenomenon in an organism or system which occurs after the organism or system has been contacted with or exposed to an exogenous agent. Pharmacologic effects may result in therapeutically effective outcomes such as the treatment, improvement of one or more symptoms, diagnosis, prevention, and delay of onset of disease, disorder, condition or infection. Measurement of such biologic phenomena may be quantitative, qualitative or relative to another biologic phenomenon. Quantitative measurements may be statistically significant. Qualitative measurements may be by degree or kind and may be at least 10%, 20%, 30%, 40%, 50%, 60%, 70%, 80%, 90% or more different. They may be observable as present or absent, better or worse, greater or less. Exogenous agents, when referring to pharmacologic effects are those agents which are, in whole or in part, foreign to the organism or system. For example, modifications to a wild type biomolecule, whether structural or chemical, would produce an exogenous agent. Likewise, incorporation or combination of a wild type molecule into or with a compound, molecule or substance not found naturally in the organism or system would also produce an exogenous agent.

The saRNA of the present invention, comprises exogenous agents. Examples of pharmacologic effects include, but are not limited to, alteration in cell count such as an increase or decrease in neutrophils, reticulocytes, granulocytes, erythrocytes (red blood cells), megakaryocytes, platelets, monocytes, connective tissue macrophages, epidermal langerhans cells, osteoclasts, dendritic cells, microglial cells, neutrophils, eosinophils, basophils, mast cells, helper T cells, suppressor T cells, cytotoxic T cells, natural killer T cells, B cells, natural killer cells, or reticulocytes. Pharmacologic effects also include alterations in blood chemistry, pH, hemoglobin, hematocrit, changes in levels of enzymes such as, but not limited to, liver enzymes AST and ALT, changes in lipid profiles, electrolytes, metabolic markers, hormones or other marker or profile known to those of skill in the art.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference in their entirety.

Prognosing: As used herein, the term "prognosing" means a statement or claim that a particular biologic event will, or is very likely to, occur in the future.

Progression: As used herein, the term "progression" or "cancer progression" means the advancement or worsening of or toward a disease or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Protein: A "protein" means a polymer of amino acid residues linked together by peptide bonds. The term, as used herein, refers to proteins, polypeptides, and peptides of any size, structure, or function. Typically, however, a protein will be at least 50 amino acids long. In some instances the protein encoded is smaller than about 50 amino acids. In this case, the polypeptide is termed a peptide. If the protein is a short peptide, it will be at least about 10 amino acid residues long. A protein may be naturally occurring, recombinant, or synthetic, or any combination of these. A protein may also comprise a fragment of a naturally occurring protein or peptide. A protein may be a single molecule or may be a multi-molecular complex. The term protein may also apply to amino acid polymers in which one or more amino acid residues are an artificial chemical analogue of a corresponding naturally occurring amino acid.

Protein expression: The term "protein expression" refers to the process by which a nucleic acid sequence undergoes translation such that detectable levels of the amino acid sequence or protein are expressed.

Purified: As used herein, "purify," "purified," "purification" means to make substantially pure or clear from unwanted components, material defilement, admixture or imperfection.

Regression: As used herein, the term "regression" or "degree of regression" refers to the reversal, either phenotypically or genotypically, of a cancer progression. Slowing or stopping cancer progression may be considered regression.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and in one embodiment, capable of formulation into an efficacious therapeutic agent.

Stabilized: As used herein, the term "stabilize", "stabilized," "stabilized region" means to make or become stable.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, in one embodiment, a mammal, or a human and most In one embodiment, a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hour period. It may be administered as a single unit dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with itself (as a homodimer) other with other molecules (as a heterodimer). Each of these complex formation is able to induce multiple regulatory function from a single transcription factor.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The phrase "a method of treating" or its equivalent, when applied to, for example, cancer refers to a procedure or course of action that is designed to reduce, eliminate or prevent the number of cancer cells in an individual, or to alleviate the symptoms of a cancer. "A method of treating" cancer or another proliferative disorder does not necessarily mean that the cancer cells or other disorder will, in fact, be completely eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an individual, is nevertheless deemed an overall beneficial course of action.

Tumor growth: As used herein, the term "tumor growth" or "tumor metastases growth", unless otherwise indicated, is used as commonly used in oncology, where the term is principally associated with an increased mass or volume of the tumor or tumor metastases, primarily as a result of tumor cell growth.

Tumor Burden: As used herein, the term "tumor burden" refers to the total Tumor Volume of all tumor nodules with a diameter in excess of 3 mm carried by a subject.

Tumor Volume: As used herein, the term "tumor volume" refers to the size of a tumor. The tumor volume in $mm^3$ is calculated by the formula: volume=$(width)^2 \times length/2$.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

The invention is further illustrated by the following non-limiting examples.

EXAMPLES

Materials and Procedures:
Transfection of saRNA
Sense and antisense strands of saRNA are synthesized. They are first annealed in a Tris-EDTA based buffer following a denaturing step at 90° C., followed by a gradual anneal step to room temperature. Cells were seeded at $1 \times 10^5$ per well in a 24-well plate and transfected using Lipofectamine 2000 (Life Technologies). Transfection was performed immediately after seeding with the indicated oligonucleotide concentration using 1 uL of Lipofectamine 2000. Cells were then transfected 24 hours later and harvested for analysis 72 hours after seeding.

RT-PCR saRNA is transfected into $1 \times 10^5$ cells. Total RNA is harvested post-transfection at 48 hours and 72 hours. The RNA isolated at 72 hours receives two sequential transfection of oligonucleotide. Total RNA is recovered using the RNeasy Mini Kit (QIAGEN) following the manufacturer's recommendation. The RNA is quantified using a QIAxpert machine (QIAGEN). 500 ng of total RNA from each sample is reverse transcribed using the One Step RT-PCR kit (Qiagen) following the manufacturer's recommendation. Relative expression levels were determined by real-time PCR using Quantifast SYBR Green Master Mix (QIAGEN) with validated Quantifast SYBR Probes from QIAGEN.

Western Blotting

Cells were seeded at $1 \times 10^5$ per well in a 24-well plate and transfected as indicated above [00346]. A pool of 4 wells per condition was used for total protein extraction. 72 hours post seeding, and prior to cell lysis, all wells were rinsed twice with ice cold PBS. RIPA lysis buffer was then added to cells (100 µL/well) containing 50 mM of Tris, 150 mM NaCl, 0.1% SDS, 0.5% sodium deoxycholate, 1% NP40, 5 mM EDTA and protease inhibitor cocktail (5 µL per 1 mL of RIPA buffer) (Sigma). Thereafter, the cells were transferred into pre-chilled tubes using a cell scraper and centrifuged gently for 15 min at 5° C. Cell debris was subsequently removed and the protein supernatant was transferred into a pre-chilled tube. The amount of protein per condition was thereafter quantified using the RC-DC Bradford Assay Kit following the manufacturer's protocol (Bio-Rad), and 6 µg of total protein was then loaded onto SDS-PAGE. Proteins are separated by gel electrophoresis. The acrylamide gels were then transferred onto polyvinylidene fluoride (PVDF) membranes. The membranes are blocked in TBS containing 4% non-fat milk for 1 hour before incubating with primary antibodies overnight at 4° C. temperature. After several washes, the blots are detected and imaged. The antibodies that were used are the following: Anti-SIRT1 antibody, ab110304 (Abcam); Anti-beta Tubulin antibody, ab6046 (Abcam); anti-rabbit-HRP, 926-80011 (LI-COR).

Example 1. Upregulation of SIRT1 mRNA Expression Through Transfection with its saRNA In Vitro HepG2 human hepatocellular carcinoma cells (ATCC) were grown in RPMI supplemented with 10% fetal bovine serum (FBS), 2 mM L-glutamine, and penicillin/streptomycin in a 5% CO2 incubator. HepG2 cells were seeded at 1×10^5 cells/well in a 24-well plate and reverse transfected (using 1 µL of Lipofectamine 2000) (Life Technologies) with 20 nM oligo (PR57) at seeding, forward transfected 24 hr later, and collected 72 hr post seeding for analysis. RNA was isolated from cultured cells using the RNeasy Mini Kit (QIAGEN) and 500 ng of RNA was reverse transcribed using the Quantitect Reverse Transcription Kit (QIAGEN). Relative expression levels were determined by qPCR and by using Livak's method of $2^{-\Delta\Delta ct}$ and is normalized to a stable house keeping gene (RPRL0).

| | |
|---|---|
| PR57 Sense: | AUAUGUCCUCCUGGGAAGA[mU][mU] (SEQ ID No. 74) |
| PR57 Antisense: | UCUUCCCAGGAGGACAUAU[mU][mU] (SEQ ID No. 96) |

[mU]: 2'-OMehtyl (2'-OMe) modified uridine.

As shown in Table 5, transfection of PR57 caused a significant increase (**p<0.01) in SIRT1 mRNA levels by 1.51 fold relative to untransfected control. The data in Table 5 represented mean data from three independent experimental runs.

TABLE 5

SIRT1-mRNA levels in HepG2 cells

| Transfections | Relative SIRT1-mRNA expression |
|---|---|
| Untransfected control | 1.00 |
| PLUG (20 nM) | 1.05 |
| SIRT1-saRNA PR57 (20 nM) | 1.51 |

Example 2. Upregulation of SIRT1 mRNA Expression in a Dose Dependent Manner In Vitro In subsequent studies increasing amounts of the saRNA (PR57) were transfected into HepG2 cells. The chosen dose escalation for SIRT1-PR57 was at 5, 10, 15 and 20 nM as shown in Table 6. Transfection of 10 nM SIRT1-PR57 demonstrated a 1.28 fold increase in SIRT1 mRNA levels (Table 6) while transfection of 15 nM and 20 nM SIRT1-PR57 caused a 1.49 and 1.48 upregulation respectively in SIRT1 mRNA levels, relative to control (mock transfected cells) (Table 6). Thus SIRT1-PR57 increased SIRT1 mRNA levels in a dose dependent manner. The data in Table 6 represented mean data from three independent experimental runs.

TABLE 6

Dose escalation of SIRT1-PR57 in HepG2 cells

| Transfections | Relative SIRT1-mRNA expression |
|---|---|
| Untransfected control | 1.02 |
| FLUC (5 nM) | 1.07 |
| FLUC (10 nM) | 1.13 |
| FLUC (15 nM) | 1.07 |
| FLUC (20 nM) | 1.09 |
| SIRT1-saRNA PR57 (5 nM) | 1.00 |
| SIRT1-saRNA PR57 (10 nM) | 1.28 |
| SIRT1-saRNA PR57 (15 nM) | 1.49 |
| SIRT1-saRNA PR57 (20 nM) | 1.48 |
| SIRT1-siRNA (10 nM) | 0.46 |

Example 3. Upregulation of SIRT1 Protein Expression

SIRT1 showed a visible increase in protein expression in HepG2 cells transfected with 20 nM SIRT1-PR57. Band densitometry indicated a 3.18 fold increase (significant *p<0.05) in protein expression induced by SIRT1-PR57, when compared to untransfected control (Table 7) and FLUC control oligonucleotide did not result in a significant increase of SIRT1 protein. siRNA control knockdown of SIRT1 showed a 0.66 fold decrease in protein expression. The data in Table 7 represents mean data from three independent experimental runs.

TABLE 7

SIRT1-protein levels in HepG2 cells

| Transfections | Reiative SIRT1-protein expression |
|---|---|
| Untransfected control | 1.00 |
| FLUC (20 nM) | 1.07 |
| SIRT1-saRNA PR57 (20 nM) | 3.18 |
| SIRT1-siRNA (10 nM) | 0.34 |

Example 4. Upregulation of SIRT1 Expression in Mouse In Vivo

Ten male C57Bl6/J, 8 week old mice are used for the experiment (control group N=5). SIRT1-saRNA reconstituted with 100 μL of RNase/Dnase free H20 are mixed with Complexation buffer and them mixed with InvivoFectamine (InvivoFectamine, Invitrogen, CA, USA) are incubated at 50° C. for 30 minutes. The InvivoFEctamine/SIRT1 saRNA complex is then used for tail vein injections. Control animals are injected with equal volume of PBS while a positive control animal received siRNA against the target gene; a total of 5 PBS, 5 positive control and 5 SIRT-1-saRNA animals are injected.

After administration, the total RNA is isolated. Frozen tissue sections from the mice are placed into metal beaded vial containing Trizol and homogenised for 1 minute. Chloroform is then added to this and mixed by vortexing vigorously for 30 sec followed by a centrifugation step at 12,000 rpm for 15 minutes at 4° C. The aqueous upper phase is then transferred into a fresh microfuge tube where RNA is precipitated using 100% Ethanol. The RNA is then purified and eluted with nuclease freewater using RNEasy RNA purification columns from Qiagen (74106). The RNA is then measured for purity (OD 260/280) and concentration using a spectrophotometer (Qiaxpert or Nanodrop).

The isolated RNA is analyzed using qRT-PCR as described in Example 1. mRNA production of the target gene is determined quantitatively and protein synthesis is measured by Western blotting as described in Example 3. The administration of saRNA using InvivoFectamine to a mouse leads to a significant increase in the SIRT-1 mRNA in tissues including the liver.

The effects of administration of saRNA on overall mice organ function may be studied. As a non-limiting example, the effects of administration of saRNA on overall liver function are determined according to the liver function markers gamma glutamyl transpeptidase, alanine aminotransferase, aspartate aminotransferase or bilirubin.

OTHER EMBODIMENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims.

The invention claimed is:

1. A synthetic isolated saRNA which up-regulates the expression of the SIRT1 gene, wherein the saRNA comprises a strand that is at least 80% complementary to a targeted sequence on the template strand of the SIRT1 gene, wherein the targeted sequence comprises SEQ ID No. 8, and wherein the saRNA comprises SEQ ID NO: 52.

2. The saRNA of claim 1, wherein the saRNA is single-stranded and comprises 14-30 nucleotides in length.

3. The saRNA of claim 2, wherein the saRNA comprises a 3' overhang.

4. The saRNA of claim 3, wherein the saRNA comprises SEQ ID NO: 96.

5. The saRNA of claim 1, wherein the saRNA is a saRNA duplex comprising an antisense strand and a sense strand, wherein the antisense strand comprises SEQ ID NO: 52, and wherein each strand is independently 14-30 nucleotides in length.

6. The saRNA of claim 5, wherein the sense strand of the saRNA comprises SEQ ID NO: 30.

7. The saRNA of claim 5, wherein the antisense strand of the saRNA comprises a 3' overhang.

8. The saRNA of claim 7, wherein the antisense strand of the saRNA comprises SEQ ID NO: 96.

9. The saRNA of claim 8, wherein the sense strand of the saRNA comprises SEQ ID NO: 74.

10. The saRNA of claim 1, wherein the saRNA comprises at least one chemical modification.

11. A pharmaceutical composition comprising the saRNA of claim 1 and at least one pharmaceutically acceptable excipient.

12. A method of up-regulating the expression of the SIRT1 gene, comprising administering the saRNA of claim 1.

13. The method of claim 12, wherein the expression of the SIRT1 gene is increased by at least 30%.

14. The method of claim 12, wherein the expression of the SIRT1 gene is increased by at least 40%.

15. The method of claim 12, wherein the expression of the SIRT1 gene is increased by at least 50%.

* * * * *

UNITED STATES PATENT AND TRADEMARK OFFICE
CERTIFICATE OF CORRECTION

| | | |
|---|---|---|
| PATENT NO. | : 11,566,246 B2 | Page 1 of 1 |
| APPLICATION NO. | : 17/046380 | |
| DATED | : January 31, 2023 | |
| INVENTOR(S) | : Hegre et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 41 days.

Signed and Sealed this
Fourteenth Day of January, 2025

Derrick Brent
*Acting Director of the United States Patent and Trademark Office*